US010350906B2

(12) United States Patent
Ito

(10) Patent No.: US 10,350,906 B2
(45) Date of Patent: Jul. 16, 2019

(54) PRINTING APPARATUS, PRINTING SYSTEM, PRINTING CONTROL METHOD AND COMPUTER-READABLE RECORDING MEDIUM

(71) Applicant: CASIO COMPUTER CO., LTD., Tokyo (JP)

(72) Inventor: Masaki Ito, Ome (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 0 days.

(21) Appl. No.: 15/882,783

(22) Filed: Jan. 29, 2018

(65) Prior Publication Data

US 2018/0257394 A1 Sep. 13, 2018

(30) Foreign Application Priority Data

Mar. 10, 2017 (JP) ................................ 2017-045649

(51) Int. Cl.
*B41J 2/36* (2006.01)
*B41J 2/355* (2006.01)
(Continued)

(52) U.S. Cl.
CPC ................ *B41J 2/355* (2013.01); *B41J 2/32* (2013.01); *B41J 2/365* (2013.01)

(58) Field of Classification Search
CPC ... B41J 2/36; B41J 2/365; B41J 2/3558; B41J 2/325; B41J 3/4075; B41J 2/32;
(Continued)

(56) References Cited

U.S. PATENT DOCUMENTS 4,376,942 A * 3/1983 Toth ........................ B41J 2/355 347/186
4,560,993 A * 12/1985 Hakoyama .............. B41J 2/365 347/182
(Continued)

FOREIGN PATENT DOCUMENTS

EP 0473191 * 3/1992 ............. B41J 2/355
JP 60-255463 * 12/1985 ............... B41J 3/20
(Continued)

OTHER PUBLICATIONS

Machine-generated translation of JP 60-255463, published on Dec. 1985.*
(Continued)

*Primary Examiner* — Huan H Tran
(74) *Attorney, Agent, or Firm* — Fitch, Even, Tabin & Flannery LLP

(57) ABSTRACT

A printing apparatus includes a thermal head and a processor. The thermal head has heat-generating elements and prints on a plurality of lines in a medium in setting periods. The processor sets a second period within each setting period. The second period is a time period for adjusting a temperature change of the heat-generating elements without printing, after a first period for printing. The processor determines a $n^{th}$ line (n: an integer of 1 or greater) among the lines based on printing data for printing the image. The $n^{th}$ line is a line estimated to have a possibility of sticking on the medium by the thermal head. The processor adjusts a temperature change of at least a part of the heat-generating elements in the second periods corresponding to at least the $n^{th}$ line and a $(n+1)^{th}$ line, to suppress the sticking.

18 Claims, 15 Drawing Sheets

(51) Int. Cl.
*B41J 2/32* (2006.01)
*B41J 2/365* (2006.01)

(58) Field of Classification Search
CPC ....... B41J 2/355; B41J 2/3555; G06K 15/024; G06K 15/028
See application file for complete search history.

(56) References Cited

U.S. PATENT DOCUMENTS

| | | | | | |
|---|---|---|---|---|---|
| 4,568,817 | A * | 2/1986 | Leng | B41J 2/38 347/172 |
| 5,025,267 | A * | 6/1991 | Schofield | B41J 2/355 347/186 |
| 5,734,411 | A * | 3/1998 | Michielsen | B41J 2/32 347/186 |
| 6,357,348 | B1 * | 3/2002 | Nakamura | B41J 2/32 101/128.4 |
| 2018/0257395 | A1 * | 9/2018 | Ogawa | B41J 2/3558 |
| 2018/0257398 | A1 * | 9/2018 | Strasemeier | A61F 13/51394 |
| 2018/0272747 | A1 * | 9/2018 | Ito | B41J 2/3555 |

FOREIGN PATENT DOCUMENTS

| | | | | |
|---|---|---|---|---|
| JP | 10-109435 | * | 10/1986 | B41J 2/32 |
| JP | H7-89115 | A | 4/1995 | |
| JP | 2009-269354 | A | 11/2009 | |
| JP | 2011-148157 | A | 8/2011 | |
| JP | 2011-178122 | A | 9/2011 | |
| JP | 2013-10200 | * | 1/2013 | B41J 2/36 |
| JP | 2013-52539 | A | 3/2013 | |

OTHER PUBLICATIONS

Machine-generated translation of JP 10-109435, published on Oct. 1996.*

* cited by examiner

FIG. 9

TB1

| WIDTH OF MEDIUM TO BE PRINTED (mm) | 3.5 | 6 | 9 | 12 | 18 | 24 | 36 | 46 |
|---|---|---|---|---|---|---|---|---|
| THRESHOLD VALUE (Byre) | 1 | 2 | 4 | 5 | 8 | 8 | 8 | 8 |

FIG. 10A

D1

| SPECIFIC LINE DATA | |
|---|---|
| 1st line | – |
| 2nd line | – |
| : | : |
| 29th line | – |
| 30th line | ○ |
| 31st line | – |
| : | : |

FIG. 10B

D2

| SPECIFIC LINE DATA | |
|---|---|
| 1st line | – |
| 2nd line | – |
| : | : |
| 30th line | ○ |
| : | : |
| 95th line | ○ |
| : | : |

FIG. 14

TB2

| APPLICATION TIME TABLE | | | |
|---|---|---|---|
| TEMPERATURE (°C) | MAIN APPLICATION TIME (μs) | HISTORY APPLICATION TIME (μs) | COUNTERMEASURE APPLICATION TIME (μs) |
| 0 | 449 | 300 | 180 |
| 1 | 443 | 296 | 177 |
| 2 | 438 | 292 | 175 |
| 3 | 432 | 288 | 173 |
| 4 | 426 | 284 | 170 |
| 5 | 421 | 280 | 168 |
| ⋮ | ⋮ | ⋮ | ⋮ |
| 28 | 287 | 191 | 115 |
| 29 | 281 | 188 | 113 |
| 30 | 274 | 183 | 110 |
| 31 | 269 | 179 | 108 |
| 32 | 265 | 177 | 106 |
| ⋮ | ⋮ | ⋮ | ⋮ |
| 60 | 190 | 126 | 76 |
| 61 | 188 | 125 | 75 |
| 62 | 186 | 124 | 74 |
| 63 | 184 | 123 | 74 |
| 64 | 183 | 122 | 73 |
| 65 | 182 | 121 | 73 |

PRINTING APPARATUS, PRINTING SYSTEM, PRINTING CONTROL METHOD AND COMPUTER-READABLE RECORDING MEDIUM

CROSS-REFERENCE TO RELATED APPLICATION

The present application claims the benefit of priority of Japanese Patent Application No. 2017-045649, filed on Mar. 10, 2017, the content of which is incorporated herein by reference.

BACKGROUND OF THE INVENTION

1. Field of the Invention

The disclosure relates to a printing apparatus, a printing system, a printing control method, and a computer-readable recording medium.

2. Description of the Related Art

In the related art, a printing apparatus configured to control application to heat-generating elements provided to a thermal head and to transfer ink applied to an ink ribbon to a medium to be printed for printing has been known.

In the printing apparatus having adopted a thermal transfer method, a phenomenon referred to as 'sticking' that the ink ribbon is stuck to the thermal head when a rapid temperature change from high temperatures to low temperatures occurs in the thermal head may occur. When the sticking occurs, it is not possible to normally wind the ink ribbon. Thereby, a region in which the printing is not normally performed is partially generated, so that a printing quality is remarkably deteriorated.

JP-A-2013-052539 discloses a thermal printer configured to prevent sticking by chopper control. The chopper control is a technology of frequently switching application/non-application to the thermal head. By performing the chopper control, it is possible to prevent the rapid temperature change of the thermal head.

When a circuit for chopper control is added to the printing apparatus, the manufacturing cost of the product increases. In the meantime, implementation of the chopper control by software makes a control program complicated and causes the size to increase.

For this reason, a control that can suppress the sticking and is simpler than the chopper control is needed in the printing apparatus.

BRIEF SUMMARY OF THE INVENTION

According to one aspect of the present invention, a printing apparatus includes a thermal head and a processor. The thermal head is configured to print an image on a plurality of lines in a medium. The thermal head includes a plurality of heat-generating elements configured to generate heat when a voltage is applied thereto, and the thermal head is controlled to print on the plurality of lines in the medium in setting periods. The processor is configured to: set a second period within each of the setting periods, the second period being a time period for adjusting a temperature change of the plurality of heat-generating elements of the thermal head without printing on the medium, and the second period being set to a timing after a first period in each of the setting periods, the first period being a time period for printing on the medium, determine a $n^{th}$ line (n: an integer of 1 or greater) among the plurality of lines in the medium based on printing data for printing the image, the $n^{th}$ line being a line estimated to have a possibility of sticking on the medium by the thermal head , and adjust a temperature change of at least a part of the plurality of heat-generating elements in the second periods corresponding to at least the $n^{th}$ line and a $(n+1)^{th}$ line as a target line group, the $(n+1)^{th}$ line is to be printed immediately after printing of the $n^{th}$ line based on the printing data, so as to suppress the sticking.

According to another aspect of the present invention, a printing system includes a printing apparatus and a computer. The printing apparatus includes a thermal head configured to print an image on a plurality of lines in a medium, and a processor configured to control the printing. The computer is provided separately from the printing apparatus. The thermal head includes a plurality of heat-generating elements configured to generate heat when a voltage is applied thereto, and the thermal head is controlled to print on the plurality of lines in the medium in setting periods. The computer is configured to: determine, as a specific line, a $n^{th}$ line (n: an integer of 1 or greater) among the plurality of lines based on printing data for printing the image, the specific line is a line estimated to have a possibility of sticking, and output specific line data for specifying the specific line to the printing apparatus. The processor is configured to: set a second period within each of the setting periods, the second period being a time period for adjusting a temperature change of the plurality of heat-generating elements of the thermal head without printing on the medium, and the second period being set to a timing after a first period in the each of the setting periods, the first period being a time period for printing on the medium, set the $n^{th}$ line and at least one line including a $(n+1)^{th}$ line which is to be printed immediately after printing of the $n^{th}$ line, as a target line group based on the specific line data, and adjust a temperature change of at least a part of the plurality of heat-generating elements in the second periods corresponding to the target line group so as to suppress the sticking.

According to another aspect of the present invention, a printing system includes a printing apparatus and a computer. The printing apparatus includes a thermal head configured to print an image on a plurality of lines in a medium, a head driving unit configured to drive the thermal head, and a processor. The computer is provided separately from the printing apparatus. The thermal head includes a plurality of heat-generating elements configured to generate heat when a voltage is applied thereto, and the thermal head is controlled to print on the plurality of lines in the medium in setting periods. The processor is configured to: set a second period within each of the setting periods, the second period being a time period for adjusting a temperature change of the plurality of heat-generating elements of the thermal head without printing on the medium, and the second period being set to a timing after a first period in the each of the setting periods, the first period being a time period for printing on the medium, drive the thermal head by the head driving unit, based on printing data for printing the plurality of lines and countermeasure data generated at the computer. The computer is configured to: determine a $n^{th}$ line (n: an integer of 1 or greater) among the plurality of lines based on printing data for printing the image, the $n^{th}$ line being a line estimated to have a possibility of sticking the thermal head to the medium, and generate the countermeasure data for adjusting a temperature change of at least a part of the plurality of heat-generating elements in the second periods of at least two lines as a target line group so as to suppress the sticking, the at least two lines including the $n^{th}$ line and a $(n+1)^{th}$ line which is to be printed immediately after printing of the $n^{th}$ line.

According to another aspect of the present invention, a printing control method is a method of a printing apparatus. The printing apparatus includes a thermal head which is configured to print an image on a plurality of lines in a medium. The thermal head includes a plurality of heat-generating elements configured to generate heat when a voltage is applied thereto, and the thermal head is controlled to print on the plurality of lines in the medium in setting periods. The printing control method comprises: setting a second period within each of the setting periods, the second period being a time period for adjusting a temperature change of the plurality of heat-generating elements of the thermal head without printing on the medium, and the second period being set to a timing after a first period in the each of the setting periods, the first period being a time period for printing on the medium, determining a $n^{th}$ line (n: an integer of 1 or greater) among the plurality of lines based on printing data for printing the image, the $n^{th}$ line being a line estimated to have a possibility of sticking, and adjusting a temperature change of at least a part of the plurality of heat-generating elements in the second periods of at least two lines as a target line group so as to suppress the sticking, the at least two lines including the $n^{th}$ line and a $(n+1)^{th}$ line which is to be printed immediately after printing of the $n^{th}$ line.

According to another aspect of the present invention, a computer-readable recording medium has a printing control program for controlling a printing apparatus recorded therein. The printing apparatus includes a thermal head which is configured to print an image on a plurality of lines in a medium. The thermal head includes a plurality of heat-generating elements configured to generate heat when a voltage is applied thereto, and the thermal head is controlled to print on the plurality of lines in the medium in setting periods. The printing control program is configured to allow a computer to: set a second period within each of the setting periods, the second period being a time period for adjusting a temperature change of the plurality of heat-generating elements of the thermal head without printing on the medium, and the second period being set to a timing after a first period in the each of the setting periods, the first period being a time period for printing on the medium, determine a $n^{th}$ line (n: an integer of 1 or greater) among the plurality of lines based on printing data for printing image, the $n^{th}$ line being a line estimated to have a possibility of sticking, and adjust a temperature change of at least a part of the plurality of heat-generating elements in the second periods of at least two lines as a target line group so as to suppress the sticking, the at least two lines including the $n^{th}$ line and a $(n+1)^{th}$ line which is to be printed immediately after printing of the $n^{th}$ line.

BRIEF DESCRIPTION OF THE SEVERAL VIEWS OF THE DRAWING

FIG. 9 exemplifies a threshold value table.

FIGS. 10A and 10B exemplifies specific line data.

FIG. 14 exemplifies an application time table.

DETAILED DESCRIPTION OF THE INVENTION

A printing apparatus in accordance with illustrative embodiments of the disclosure will be described in detail with reference to the drawings.

[First Illustrative Embodiment]

Figure 1:
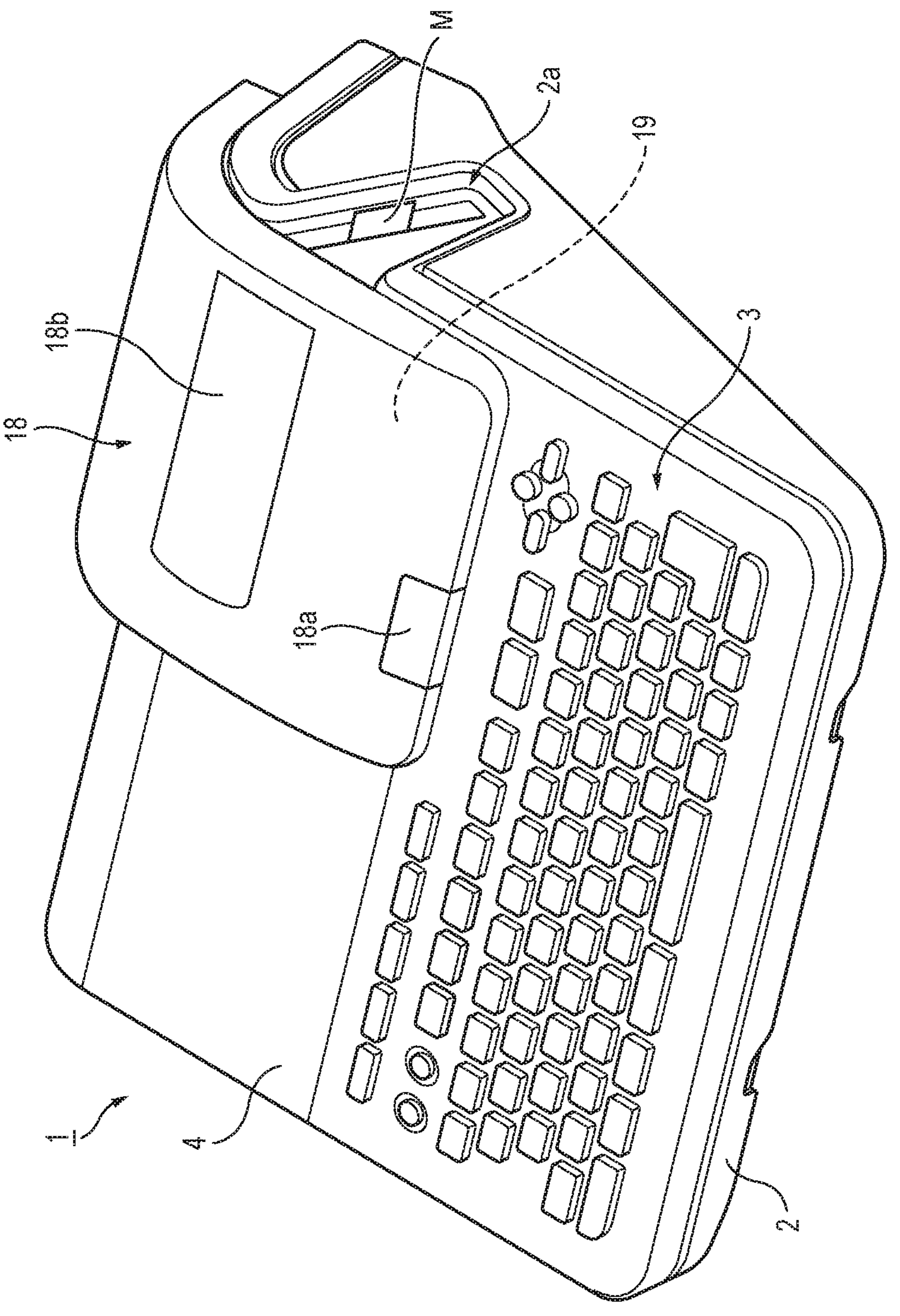
FIG. 1 is a perspective view of a printing apparatus 1.

FIG. 1 is a perspective view of a printing apparatus 1 in accordance with a first illustrative embodiment.

The printing apparatus 1 is a printing apparatus including a thermal head configured to perform printing on a medium to be printed. For example, the printing apparatus 1 is a label printer configured to perform printing on a long medium to be printed M in a single-path manner.

In the below, the label printer of a thermal transfer method using an ink ribbon will be exemplified. However, the printing method is not particularly limited. The printing method may be any method in which a sticking may occur. For example, the printing method may be a thermosensitive method using a heat-sensitive paper.

The medium to be printed M is a long tape member including a base material having an adhesive layer and a release paper releasably adhered to the base material so as to cover the adhesive layer. In the meantime, the medium to be printed M may be a tape member without release paper.

As shown in FIG. 1, the printing apparatus 1 includes an apparatus housing 2, an input unit 3, a display device 4, an opening and closing cover 18, and a cassette storage unit 19.

The input unit 3, the display device 4, and the opening and closing cover 18 are arranged on an upper surface of the apparatus housing 2.

Although not shown, the apparatus housing 2 is provided with a power supply cord connection terminal, an external device connection terminal, a storage medium insertion port, and the like.

The input unit 3 includes a variety of keys such as an input key, arrow keys, a conversion key, an enter key, and the like.

The display device 4 is a liquid crystal display panel, for example, and is configured to display letters corresponding to an input from the input unit 3, a selection menu for diverse setting, messages relating diverse processing, and the like. During the printing, a content (hereinafter, referred to as printing content) such as a letter, a figure and the like, which are instructed to be printed on the medium to be printed M, is displayed on the display device 4, and a progressing status of printing processing may be further displayed thereon.

In the meantime, the display device 4 may be provided with a touch panel unit. In this case, the display device 4 may be considered as a part of the input unit 3.

The opening and closing cover 18 is arranged to be openable and closable at an upper part of the cassette storage unit 19. The opening and closing cover 18 is opened when a button 18*a* is pushed.

The opening and closing cover 18 is provided with a window 18*b* so as to check whether a tape cassette 30 (refer to FIG. 2) is accommodated in the cassette storage unit 19 with naked eyes even at a state where the opening and closing cover 18 is closed.

A side surface of the apparatus housing 2 is formed with a discharge port 2*a*.

The medium to be printed M on which the printing has been performed in the printing apparatus 1 is discharged from the discharge port 2*a* to an outside of the apparatus.

Figure 2:
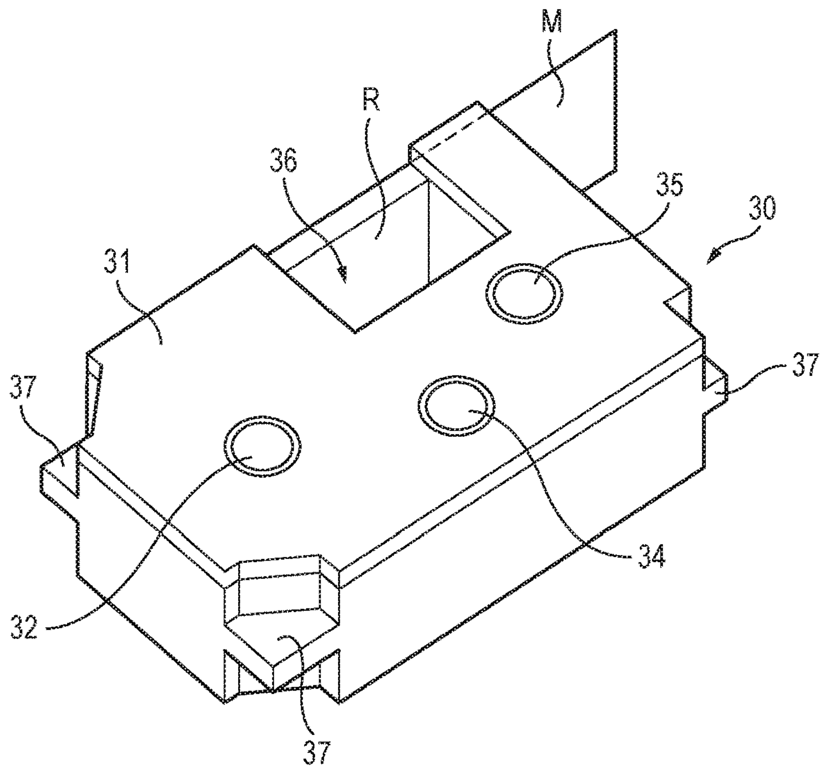
FIG. 2 is a perspective view of a tape cassette 30 that is to be accommodated in the printing apparatus 1.

FIG. 2 is a perspective view of a tape cassette 30 that is to be accommodated in the printing apparatus 1.

Figure 3:
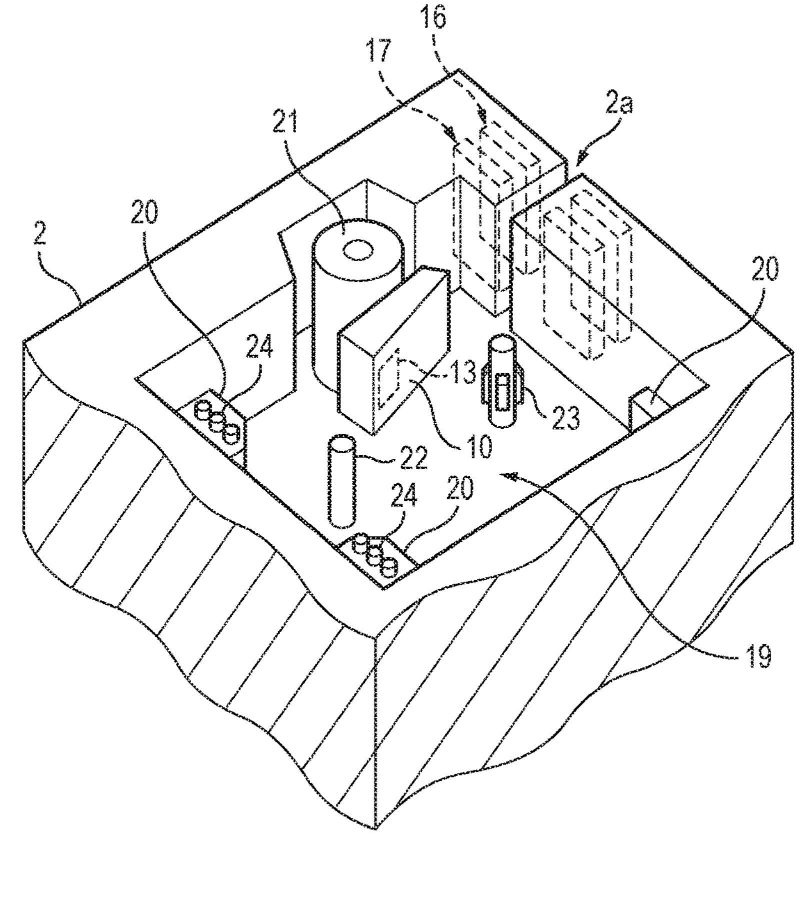
FIG. 3 is a perspective view of a cassette storage unit 19 of the printing apparatus 1.

FIG. 3 is a perspective view of the cassette storage unit 19 of the printing apparatus 1.

Figure 4:
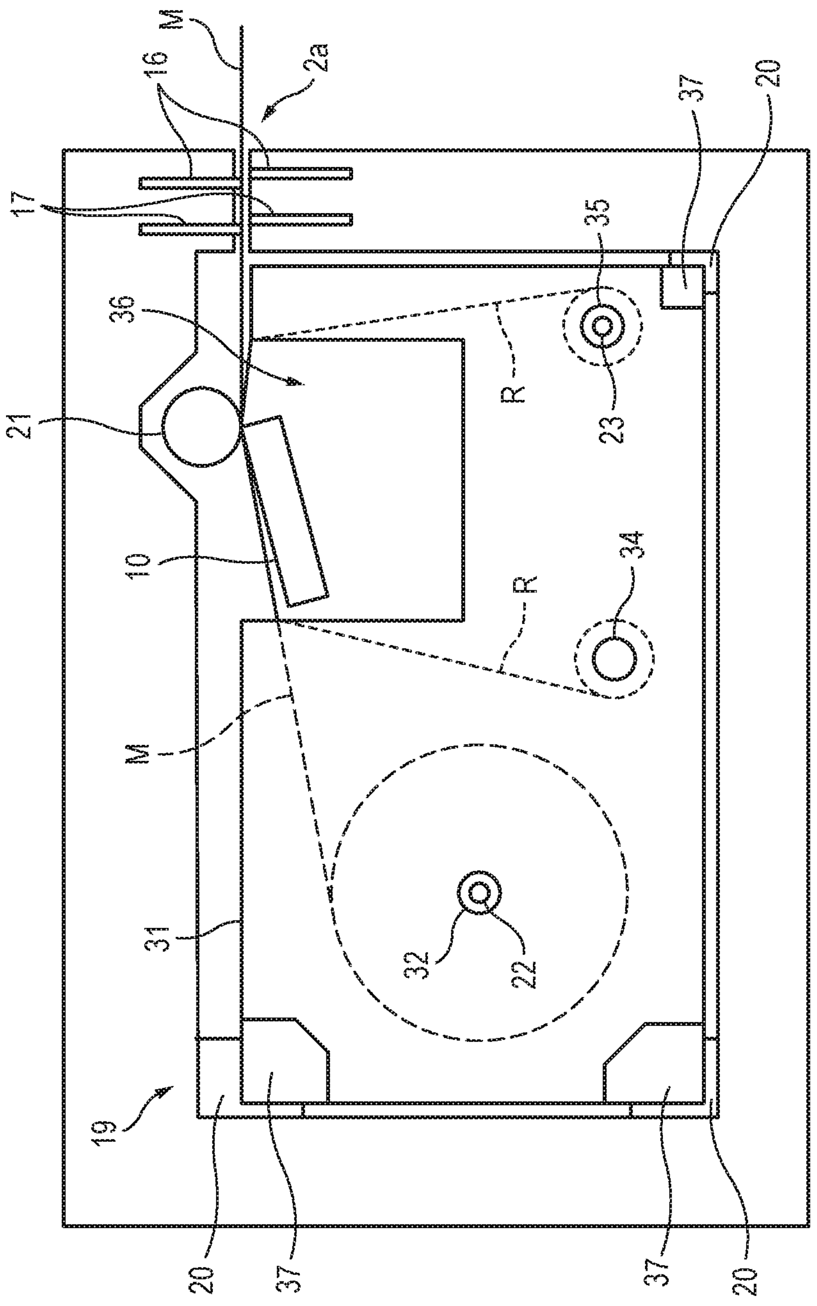
FIG. 4 is a sectional view of the printing apparatus 1.

FIG. 4 is a sectional view of the printing apparatus 1.

The tape cassette 30 shown in FIG. 2 is accommodated in the cassette storage unit 19 shown in FIG. 3 so as to be freely mounted and demounted.

FIG. 4 depicts a state where the tape cassette 30 is accommodated in the cassette storage unit 19.

As shown in FIG. 2, the tape cassette 30 has a cassette case 31 configured to accommodate therein the medium to be printed M and an ink ribbon R and formed with a thermal head insertion part 36 and engaging parts 37.

The cassette case 31 is provided with a tape core 32, an ink ribbon supply core 34, and an ink ribbon winding core 35.

The medium to be printed M is wound on the tape core 32 in the cassette case 31 in a roll shape.

The ink ribbon R for thermal transfer is wound on the ink ribbon supply core 34 within the cassette case 31 in a roll shape at a state where a tip end thereof is wound on the ink ribbon winding core 35.

As shown in FIG. 3, the cassette storage unit 19 of the apparatus housing 2 is provided with a plurality of cassette receiving parts 20 for supporting the tape cassette 30 at a predetermined position.

The cassette receiving part 20 is provided with a tape width detection switch 24 for detecting a width of a tape (medium to be printed M) to be accommodated in the tape cassette 30.

The tape width detection switch 24 is a width detection unit configured to detect a width of the medium to be printed M based on a shape of the cassette.

The cassette storage unit 19 is further provided with a thermal head 10 having a plurality of heat-generating elements and configured to perform printing on the medium to be printed M, a platen roller 21, which is a conveyance unit configured to convey the medium to be printed M, a tape core engaging shaft 22, and an ink ribbon winding drive shaft 23. In the thermal head 10, a thermistor 13 is embedded. The thermistor 13 is a head temperature measuring unit configured to measure a temperature of the thermal head 10.

As shown in FIG. 4, at a state where the tape cassette 30 is accommodated in the cassette storage unit 19, the engaging parts 37 provided to the cassette case 31 are supported to the cassette receiving parts 20 provided to the cassette storage unit 19. Then, the thermal head 10 is inserted in the thermal head insertion part 36 formed in the cassette case 31.

The tape core engaging shaft 22 is engaged with the tape core 32 of the tape cassette 30. The ink ribbon winding drive shaft 23 is engaged with the ink ribbon winding core 35.

When a printing instruction is input to the printing apparatus 1, the medium to be printed M is supplied from the tape core 32 by rotation of the platen roller 21.

At this time, the ink ribbon winding drive shaft 23 is synchronously rotated with the platen roller 21, so that the ink ribbon R is supplied from the ink ribbon supply core 34 together with the medium to be printed M. Thereby, the medium to be printed M and the ink ribbon R are conveyed with being superimposed on each other.

When passing between the thermal head 10 and the platen roller 21, the ink ribbon R is heated by the thermal head 10, so that the ink is transferred to the medium to be printed M and the printing is thus performed.

The used ink ribbon R, which has passed between the thermal head 10 and the platen roller 21 and the ink thereof has been transferred to the medium to be printed M, is wound to the ink ribbon winding core 35.

In the meantime, the printed medium to be printed M having passed between the thermal head 10 and the platen roller 21 is cut by a half-cut device 16 and a full-cut device 17 and is then discharged from the discharge port 2*a*.

Figure 5:
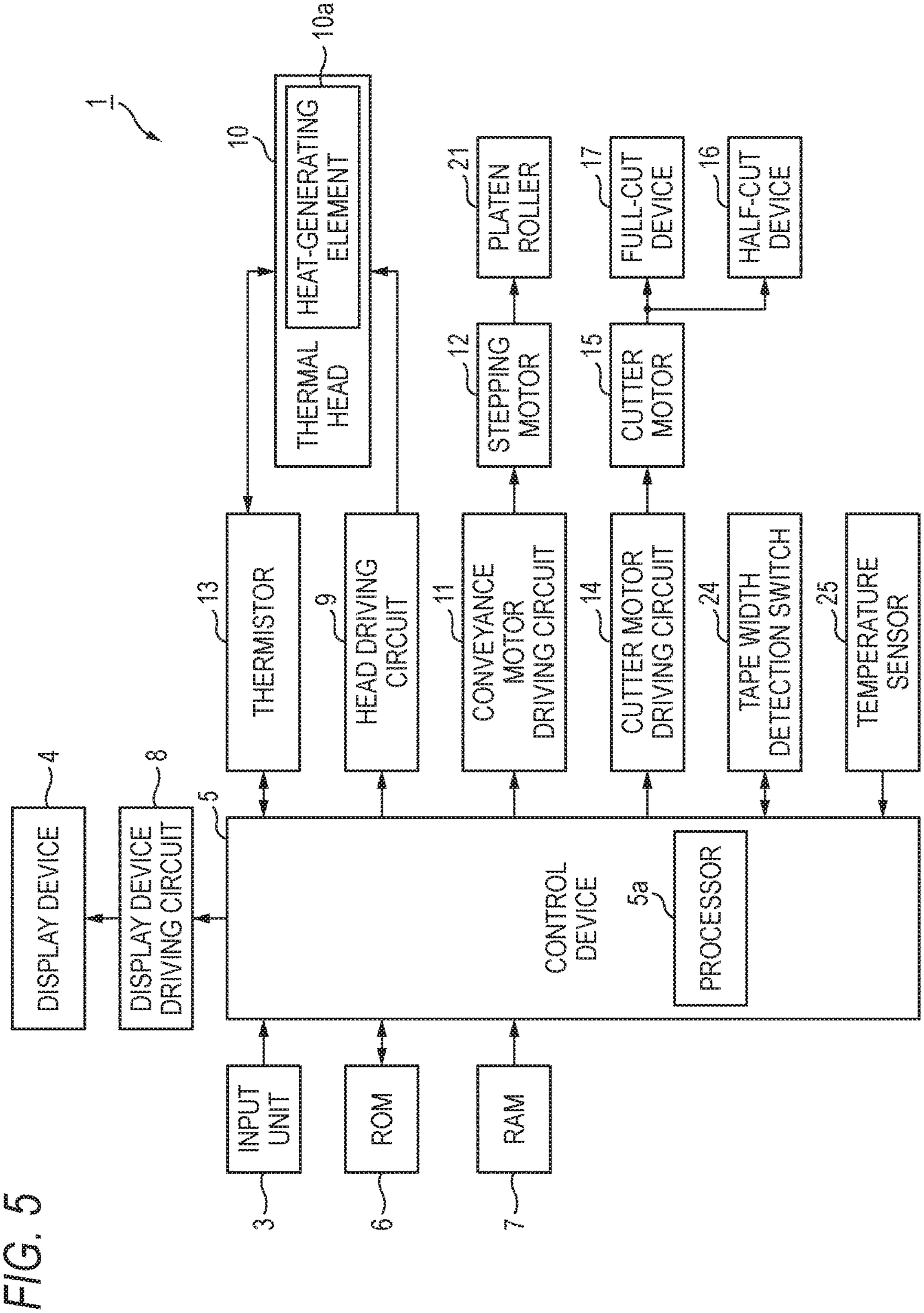
FIG. 5 is a block diagram depicting a hardware structure of the printing apparatus 1.

FIG. 5 is a block diagram depicting a hardware structure of the printing apparatus 1.

The printing apparatus 1 includes a control device 5, a ROM (Read Only Memory) 6, a RAM (Random Access Memory) 7, a display device driving circuit 8, a head driving circuit 9, a conveyance motor driving circuit 11, a stepping motor 12, a cutter motor driving circuit 14, a cutter motor 15, and a temperature sensor 25, in addition to the input unit 3, the display device 4, the thermal head 10, the thermistor 13, the half-cut device 16, the full-cut device 17, the platen roller 21, and the tape width detection switch 24.

In the meantime, at least the control device 5, the ROM 6 and the RAM 7 configure a computer of the printing apparatus 1.

The control device 5 includes a processor 5*a* such as a CPU (Central Processing Unit) and the like, for example. The control device 5 is configured to develop programs stored in the ROM 6 into the RAM 7 and to execute the same, thereby controlling operations of the respective units of the printing apparatus 1.

The control device 5 functions as an estimation unit configured to estimate a line having a relatively high possibility of occurrence of sticking (hereinafter, referred to as 'specific line'), based on printing data.

The control device 5 functions as a data generation unit configured to generate countermeasure data for suppressing occurrence of sticking, too.

The control device 5 functions as a head control unit configured to generate a strobe signal, which is an example of the control signal for designating a first application control time period (a first period) for performing printing on the medium to be printed M and a second application control time period (a second period) for adjusting a temperature change of the thermal head 10 without performing printing on the medium to be printed M, too.

The control device 5 is configured to supply at least the strobe signal, the printing data and the countermeasure data to the head driving circuit 9, and to control the thermal head 10 via the head driving circuit 9.

The control device 5 functions as a conveyance control unit configured to control the platen roller 21, too.

Also, the control device 5 functions as a cut control unit configured to control a cut device, too.

In the meantime, the application control time period indicates a time period for which the strobe signal is ON.

The first application control time period is a time period for which application or non-application to a plurality of heat-generating elements 10*a* of the thermal head 10*a* is set in correspondence to printing data, and is a time period for which a color is formed on the medium to be printed M in correspondence to printing data. That is, the printing data is data for designating application or non-application to the plurality of heat-generating elements 10*a* for the first application control time period.

Herein, the color formation indicates that green ink is transferred from the ink ribbon R to the medium to be printed M and the medium to be printed M is thus colored, and/or that the medium to be printed M forms a color by itself.

The second application control time period is a time period for which application or non-application to the plurality of heat-generating elements 10*a* of the thermal head 10*a* is set in correspondence to countermeasure data, and is a time period for which a temperature change (particularly, temperature lowering) of the thermal head 10 is adjusted in correspondence to the countermeasure data without the color formation of the medium to be printed M.

That is, the countermeasure data is data for designating application or non-application to the plurality of heat-generating elements 10*a* for the second application control time period.

The second application control time period is a time period that is temporally spaced from the first application control time period, is a time period that is set as timing temporally later than the first application control time period with a non-application control time period, for which the plurality of heat-generating elements 10*a* of the thermal head 10 is not energized, being interposed therebetween, and is a time period temporally shorter than the first application control time period.

The second application control time period is a time period having time of about 30% to 50% of the first application control time period, and is time from 100 μsec to 200 μsec.

In the ROM 6, a printing program for performing the printing on the medium to be printed M, and a variety of data (for example, fonts, an application table, a threshold value table and the like) necessary to execute the printing program are stored.

The ROM 6 functions as a storage medium in which a program, which can be read by the control device 5, is stored.

The RAM 7 includes a printing data storage part in which data (hereinafter, referred to as 'printing data') indicative of a pattern of printing content is stored. Also, the RAM 7 includes a display data storage part in which display data is stored.

The display device driving circuit 8 is configured to control the display device 4, based on the display data stored in the RAM 7.

The display device 4 may display the printing content in such an aspect that a user can recognize a progressing status of printing processing, under control of the display device driving circuit 8, for example.

The head driving circuit 9 is a head driving unit configured to drive the thermal head 10, based on the strobe signal, which is a control signal to be supplied from the control device 5, the printing data and the countermeasure data.

More specifically, during an application control time period in which the strobe signal (control signal) is ON, a voltage to be supplied to the plurality of heat-generating elements 10*a* is energized or de-energized based on the printing data and the countermeasure data.

The thermal head 10 is a printing head having the plurality of heat-generating elements 10*a* aligned in a main scanning direction and configured to print on a plurality of lines in the medium to be printed M.

The head driving circuit 9 is configured to enable the heat-generating elements 10*a* to generate heat and to heat the ink ribbon R by selectively energizing the voltage to be supplied to the heat-generating elements 10*a*, in correspondence to the printing data and the countermeasure data, during the application control time period of the strobe signal supplied from the control device 5. Thereby, the thermal head 10 performs printing line by line on the medium to be printed M by the thermal transfer. That is, the printing apparatus 1 is a thermal line printer.

The conveyance motor driving circuit 11 is configured to drive the stepping motor 12. The stepping motor 12 is configured to rotate the platen roller 21. The platen roller 21 is a conveyance unit configured to rotate by power from the stepping motor 12 and to convey the medium to be printed M in a longitudinal direction (sub-scanning direction) of the medium to be printed M.

The cutter motor driving circuit 14 is configured to drive the cutter motor 15.

The half-cut device 16 and the full-cut device 17 are configured to operate by power from the cutter motor 15, thereby half-cutting or full-cutting the medium to be printed M.

The full cut is an operation of cutting the base material of the medium to be printed M together with the release paper along the width direction, and the half cut is an operation of cutting only the base material along the width direction.

The temperature sensor 25 is an environment temperature measuring unit configured to measure a temperature around the printing apparatus 1, as an environment temperature.

Figure 6:
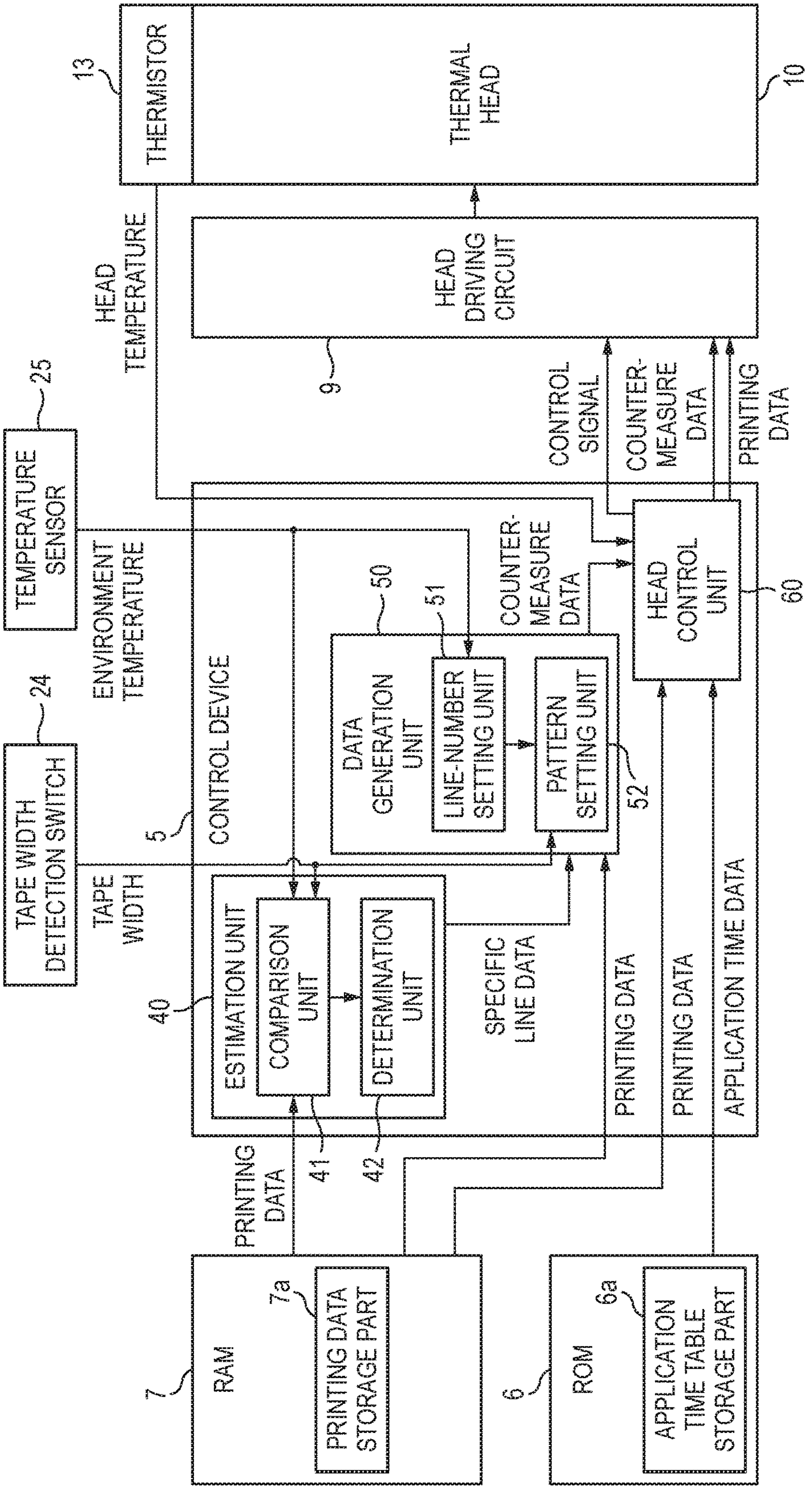
FIG. 6 is a block diagram depicting a functional structure of the printing apparatus 1.

FIG. 6 is a block diagram depicting a functional structure of the printing apparatus 1.

FIG. 6 mainly depicts a functional structure of the control device 5 included in the printing apparatus 1.

The control device 5 includes an estimation unit 40, a data generation unit 50, and a head control unit 60. In the meantime, the estimation unit 40, the data generation unit 50, and the head control unit 60 may be configured by a dedicated circuit, respectively, or may be implemented by execution of programs stored in the ROM 6.

The estimation unit 40 is configured to estimate a specific line having a relatively high possibility of occurrence of sticking by specifying a line having a possibility that a temperature of the thermal head 10 will rapidly decrease at the line, based on the printing data.

Specifically, the estimation unit is configured to estimate a line at which the sticking will occur by comparing two or more printing line data of a plurality of printing line data included in the printing data.

In the meantime, the printing data that is to be used by the estimation unit 40 is read out from a printing data storage part 7*a* of the RAM 7.

The specific line may be any line for which it is estimated that the sticking will occur, and the estimation unit may be configured to estimate a line for which it is estimated that the sticking will occur, as the specific line.

More specifically, the estimation unit 40 includes a comparison unit 41, and a determination unit 42.

The comparison unit 41 is configured to compare two printing line data, which corresponds to two lines to be printed with being adjacent to each other, of the plurality of printing line data.

The determination unit 42 is configured to determine a line having a relatively high possibility of occurrence of sticking, as the specific line, based on a comparison result of the comparison unit 41.

That is, the estimation unit 40 is configured to estimate the specific line, based on the comparison result of the two printing line data, which corresponds to two lines to be printed with being adjacent to each other. The reason is that it is possible to expect a rapid temperature change, which will occur between two lines to be printed with being adjacent to each other, by comparing the two printing line data corresponding to two lines to be printed with being adjacent to each other.

The comparison unit 41 may be configured to compare a number of printing dots, which are specified based on one of two printing line data corresponding to two lines to be printed with being adjacent to each other and are set to be printed on the medium to be printed M by enabling the heat-generating elements 10*a* of the thermal head 10 to generate heat, and a number of printing dots, which are specified based on the other of two printing line data corresponding to two lines to be printed with being adjacent to each other, for example. The reason is that it is possible to expect temperature lowering of the thermal head 10 by comparing the numbers of printing dots.

The comparison unit 41 may also be configured to compare a number of printing dot groups, which are printing dots specified based on one of two printing line data corresponding to two lines to be printed with being adjacent to each other and continuously aligned by a predetermined number, and a number of printing dot groups, which are specified based on the other of two printing line data corresponding to two lines to be printed with being adjacent to each other, for example. When a plurality of printing dots is grouped, an influence on the temperature of the thermal head 10 may be increased, as compared to printing dots that are apart from each other. For this reason, it is possible to expect the temperature lowering of the thermal head 10 with higher precision by comparing the numbers of printing dot groups, each of which is a set of the plurality of printing dots.

The determination unit 42 may set a threshold value for a ratio of the numbers of printing dots or the numbers of printing dot groups or may set a threshold value for a decrease number of the number of printing dots or the number of printing dot groups, for example.

The determination unit 42 may determine that there is a relatively high possibility of occurrence of sticking, when the ratio or decrease number is equal to or greater than the threshold value.

In the meantime, the threshold value may be a preset value or may be a value that is set based on the environment temperature measured by the temperature sensor 25.

The lower the environment temperature, the sticking is generally more likely to occur. Therefore, when setting the threshold value based on the environment temperature, it is preferable to reduce the threshold value as the environment temperature is lower. Thereby, it is possible to further suppress the sticking.

The threshold value may also be set based on a width of the medium to be printed M detected by the tape width detection switch 24. For example, when a width of the medium to be printed M is relatively narrow, a line at which the sticking will occur may be set using a smaller threshold value, as compared to the medium to be printed M having a relatively wide width. The reason is that when a width of the medium to be printed M is narrow, only a narrow region in the thermal head 10 is heated, so that the thermal head 10 is likely to be rapidly cooled and the sticking is thus likely to occur.

The estimation unit 40 is configured to output data (hereinafter, referred to as 'specific line data') for specifying the estimated specific line to the data generation unit 50.

The data generation unit 50 is configured to generate countermeasure data for designating application or non-application to the plurality of heat-generating elements 10*a* during the second application control time period, and to output the same to the head control unit 60.

The countermeasure data includes a plurality of countermeasure line data corresponding to the plurality of printing line data included in the printing data.

In the printing apparatus 1, the heat-generating elements 10*a* are enabled to generate the heat based on the countermeasure data, which is data different from the printing data, for a time period in which a temperature lowering, which may highly cause the sticking, is expected. Thereby, the rapid temperature lowering of the thermal head 10 is suppressed, so that the occurrence of sticking is suppressed.

At this time, the second application control time period in which the heat-generating elements 10*a* are enabled to generate the heat based on the countermeasure data is set to be shorter than the first application control time period so that a color is not formed on the medium to be printed M.

To this end, the data generation unit 50 is configured to generate countermeasure data for designating application of a voltage to the heat-generating elements 10*a* included in the thermal head 10 during the second application control time period not only for the specific line but also for at least one line, which is to be printed continuously from the specific line after the specific line.

Thereby, since it is possible to securely suppress the rapid temperature lowering, it is possible to sufficiently suppress the occurrence of sticking.

Herein, two or more lines including the specific line and at least one line, which is to be printed continuously from the specific line after the specific line, are hereinafter referred to as 'countermeasure target line group'.

That is, the data generation unit 50 is configured to set, as a countermeasure target line group, at least a $n^{th}$ line (n: an integer of 1 or greater), for which it is estimated that the sticking will occur, and a $(n+1)^{th}$ line to be printed continuously from the $n^{th}$ line of a plurality of lines based on the printing data for printing the plurality of lines, and to generate countermeasure line data for controlling so that a voltage is to be applied to at least a part of the plurality of heat-generating elements 10*a* for the second application control time period at each line included in the countermeasure target line group.

More specifically, the data generation unit 50 includes a line-number setting unit 51 and a pattern setting unit 52.

The line-number setting unit 51 is configured to set a number of lines of the plurality of lines, i.e., a number of lines, which are to be included in the countermeasure target line group.

The pattern setting unit 52 is configured to set the heat-generating elements to which a voltage is to be applied for the second application control time period.

The line-number setting unit 51 may be configured to set a number of lines, which are to be included in the countermeasure target line group, as a preset number.

The line-number setting unit 51 may be configured to set the number of lines, based on the environment temperature measured by the temperature sensor 25.

The line-number setting unit 51 may be configured to set the number of lines, based on the printing data.

The line-number setting unit 51 may be configured to set the number of lines, based on a width of the medium to be printed M detected by the tape width detection switch 24.

The line-number setting unit 51 may be configured to set the number of lines, based on at least one of the environment temperature, the printing data and the width of the medium to be printed M.

The lower the environment temperature, the sticking is generally more likely to occur. Therefore, when the line-number setting unit 51 is configured to set the number of lines based on the environment temperature, it is preferable to increase the number of lines as the environment temperature is lower, so as to suppress the rapid temperature lowering. Thereby, it is possible to suppress the occurrence of sticking, regardless of the environments in which the printing apparatus 1 is located.

On the other hand, in an environment where the environment temperature is high, the sticking is difficult to occur. For this reason, when the environment temperature is higher than a preset threshold value (for example, 40° C.), the line-number setting unit 51 sets the number of lines to zero (0), so that the application control may be omitted during the second application control time period.

When the voltage is applied to the sufficient number of heat-generating elements 10*a* for the first application control time period at lines subsequent to the specific line, since the temperature lowering does not occur at the lines, it can be determined that the application control can be omitted for the second application control time period.

Therefore, the line-number setting unit 51 may be configured to calculate how many lines (hereinafter, referred to as low-printing rate lines) having a number of printing dots equal to or lower than a threshold value are continuously aligned at a plurality of lines to be printed continuously from the specific line after the specific line, based on the printing data, and to set the number of lines to be included in the countermeasure target line group based on the calculated number of low-printing rate lines to continue.

The line-number setting unit 51 may be configured to set the number of lines based on the width of the medium to be printed M. For example, when the width of the medium to be printed M is greater than a threshold value (for example, 18 mm), the line-number setting unit 51 sets the number of lines to zero (0), in consideration of the limit on a current capacity of a power supply circuit configured to apply a voltage to the thermal head 10, and only when the width of the medium to be printed M is equal to or smaller than the threshold value, the application control may be performed for the second application control time period.

The pattern setting unit 52 may be configured to set the heat-generating elements to which a voltage is to be applied for the second application control time period, based on the width of the medium to be printed M detected by the tape width detection switch 24.

The pattern setting unit 52 may be configured to specify the heat-generating elements facing the medium to be printed M, based on the width of the medium to be printed M, and to set the specified heat-generating elements as the heat-generating elements to which a voltage is to be applied for the second application control time period, for example.

The pattern setting unit 52 may be configured to specify the heat-generating elements facing a printing region except for a blank part of the medium to be printed M, based on the width of the medium to be printed M, and to set the specified heat-generating elements as the heat-generating elements to which a voltage is to be applied for the second application control time period.

Thereby, since it is possible to enable all the heat-generating elements, which are to be used for printing for the second application control time period, to concurrently generate the heat, it is possible to heat not only a place, at which it is expected that the sticking will occur, in the specific line but also a surrounding of the place.

Therefore, it is possible to effectively suppress the rapid temperature lowering of the place, at which it is expected that the sticking will occur, by the heat generated at the place and the surrounding thereof. For this reason, it is possible to sufficiently suppress the occurrence of sticking for the short application time period (second application time).

The pattern setting unit 52 may be configured to set preset heat-generating elements, as the heat-generating elements to which a voltage is to be applied for the second application control time period.

The pattern setting unit 52 may be configured to set the heat-generating elements to which a voltage is to be applied for the second application control time period, so as to enable many heat-generating elements to concurrently generate heat for the second application control time period within a range not exceeding the limit on the current capacity of the power supply circuit configured to apply a voltage to the thermal head 10.

The pattern setting unit 52 may be configured to set the heat-generating elements to which a voltage is to be applied for the second application control time period, based on the printing data.

The pattern setting unit 52 is configured to set at least heat-generating elements corresponding to a place, at which it is expected that the sticking will occur, in the specific line, as the heat-generating elements to which a voltage is to be applied for the second application control time period.

The head control unit 60 is configured to generate a strobe signal, which is a control signal for designating the first application control time period and the second application control time period, and to output the same to the head driving circuit 9.

That is, the head control unit 60 is configured to set the first application control time period for performing printing on the medium to be printed M within one line period (setting period) for printing each of the plurality of lines, and to set the second application control time period for adjusting a temperature change of the thermal head 10 without performing printing on the medium to be printed M within the one line period (setting period) and temporally spaced from the first application control time period.

More specifically, the head control unit 60 is configured to calculate application times of the first application control time period and the second application control time period, based on the application time data read out from the application time table storage part 6*a* of the ROM 6 and the head temperature measured with the thermistor 13.

Then, the head control unit 60 is configured to output the strobe signal (control signal) corresponding to the application times, the printing data and the countermeasure data generated at the data generation unit 60 to the head driving circuit 9. In the meantime, the application time is a temporal length of the application time period.

According to the printing apparatus 1 configured as described above, it is possible to suppress the rapid temperature lowering of the thermal head 10 by controlling the application to the plurality of heat-generating elements 10*a* for the second application control time period, based on the countermeasure data.

Therefore, it is possible to suppress the occurrence of sticking with the simple control.

For this reason, it is possible to avoid deterioration of the printing quality, which is caused due to the sticking.

In particular, in the thermal head 10 corresponding to the high-speed printing, the heat-generating elements are relatively likely to be warmed and are also likely to be cooled, so that the sticking is likely to occur. However, according to the above technology, it is possible to considerably suppress the occurrence of sticking.

Figure 7:
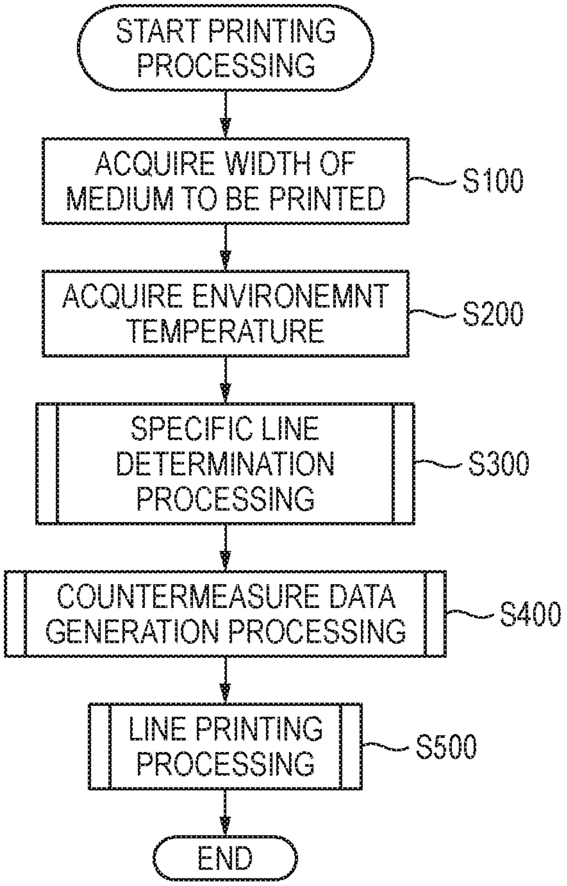
FIG. 7 is a flowchart of printing processing.

FIG. 7 is a flowchart of printing processing.

Figure 8:
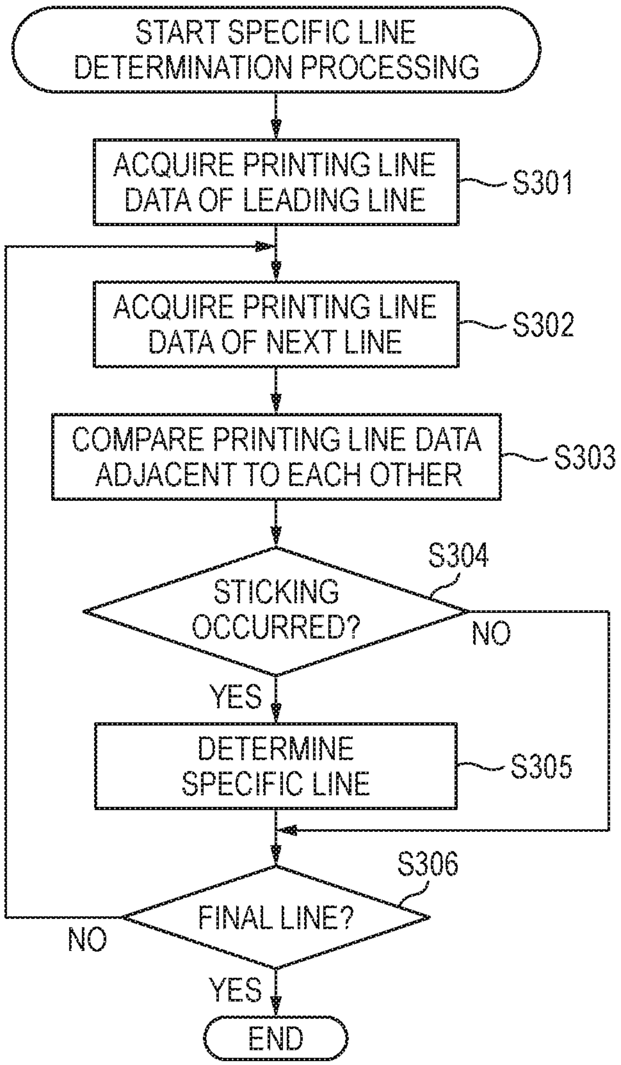
FIG. 8 is a flowchart of specific line determination processing.

FIG. 8 is a flowchart of specific line determination processing.

FIG. 9 exemplifies a threshold value table.

FIGS. 10A and 10B exemplifies specific line data.

Figure 11:
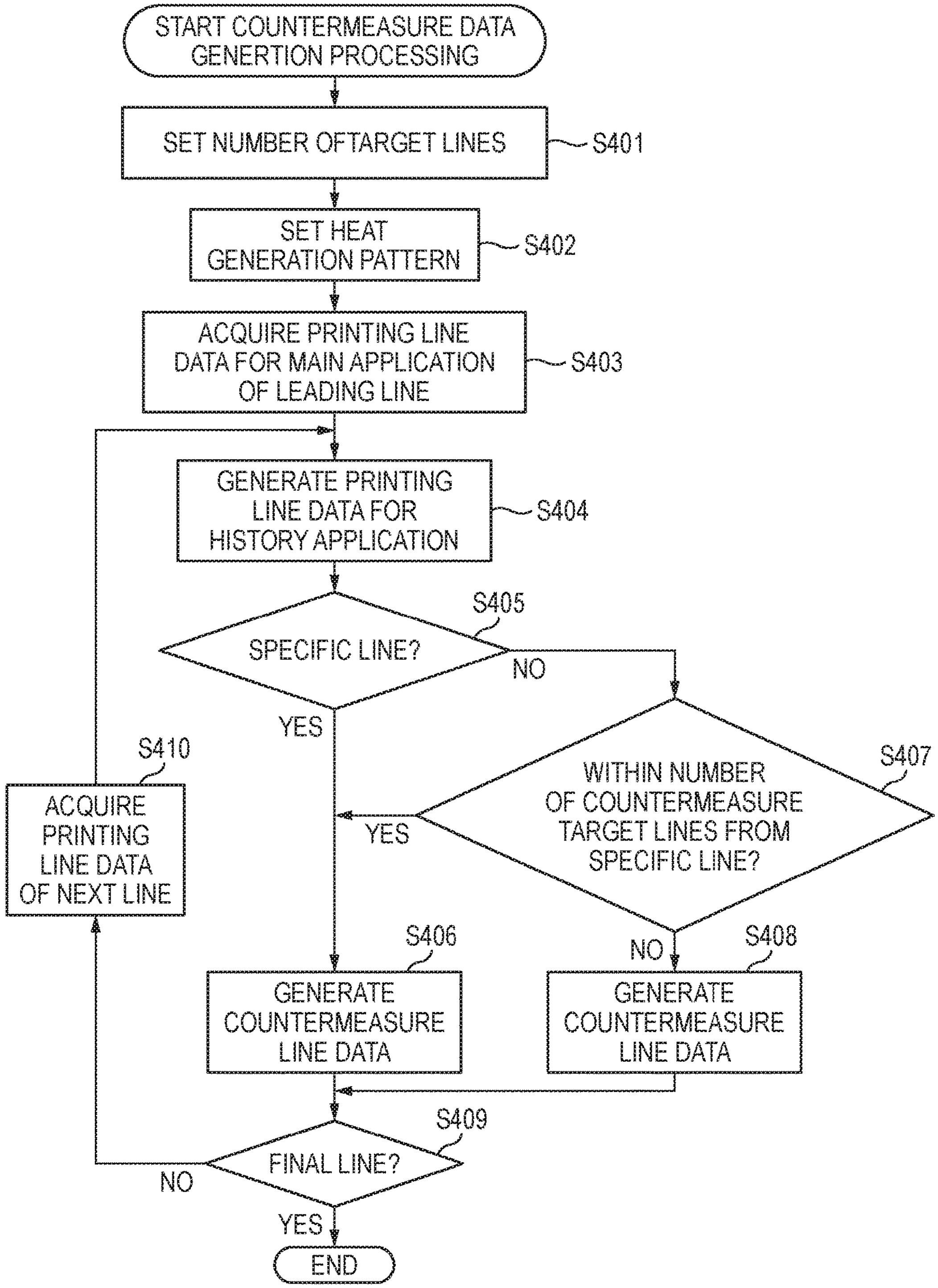
FIG. 11 is a flowchart of countermeasure data generation processing.

FIG. 11 is a flowchart of countermeasure data generation processing.

Figure 12:
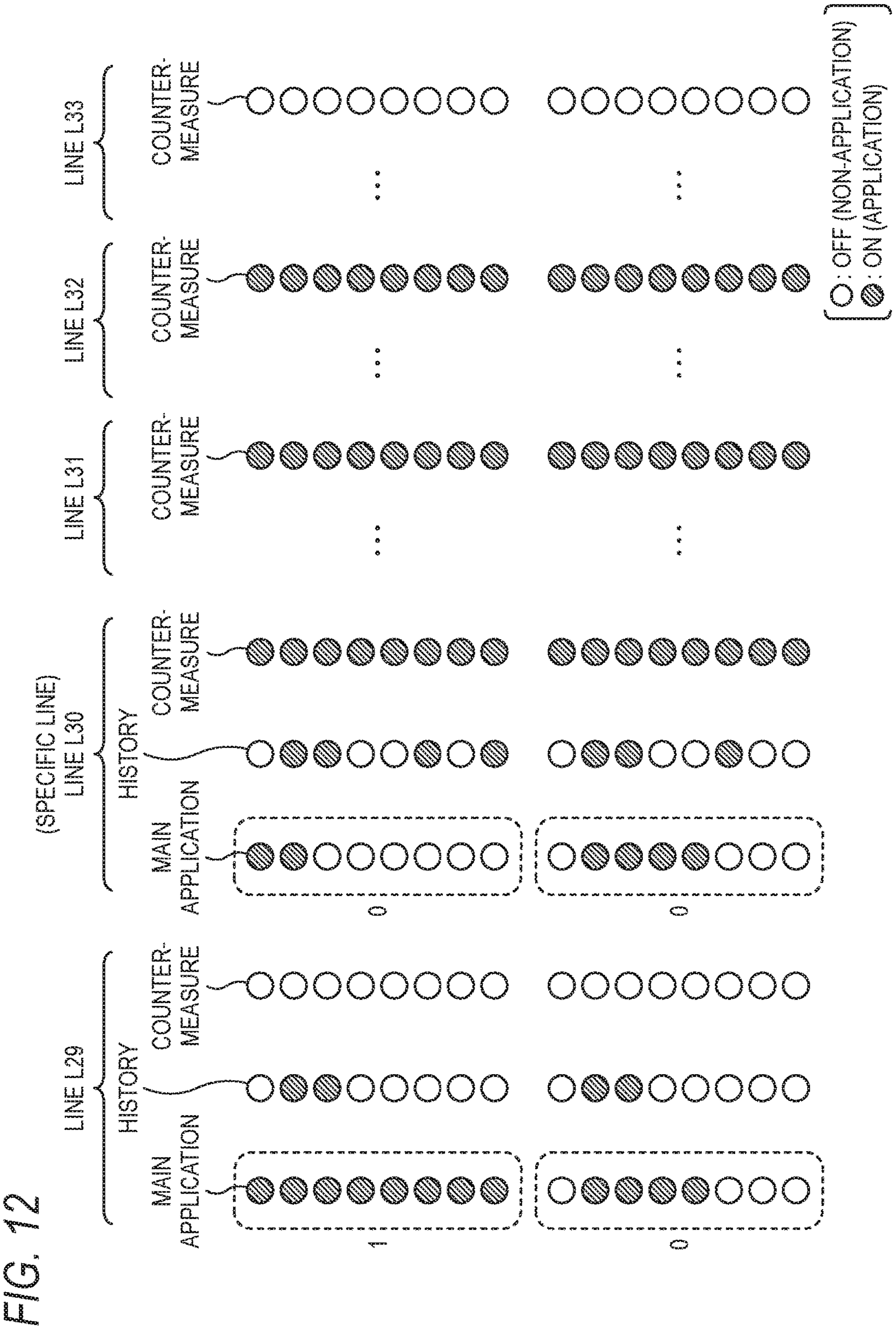
FIG. 12 exemplifies countermeasure data that is to be generated in the countermeasure data generation processing.

FIG. 12 exemplifies countermeasure data that is to be generated in the countermeasure data generation processing.

Figure 13:
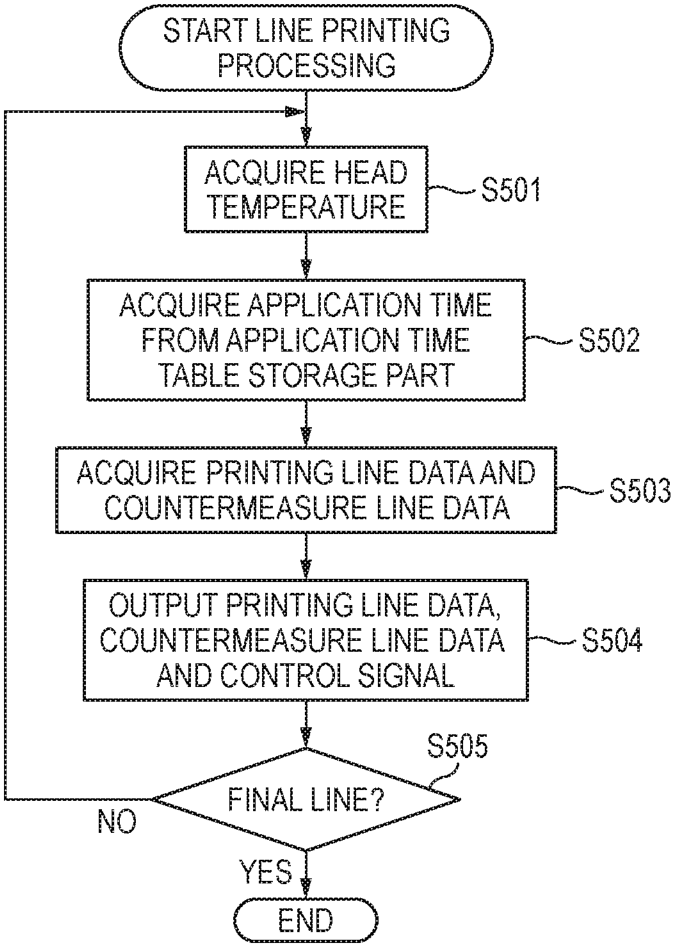
FIG. 13 is a flowchart of line printing processing.

FIG. 13 is a flowchart of line printing processing.

FIG. 14 exemplifies an application time table.

Figure 15:
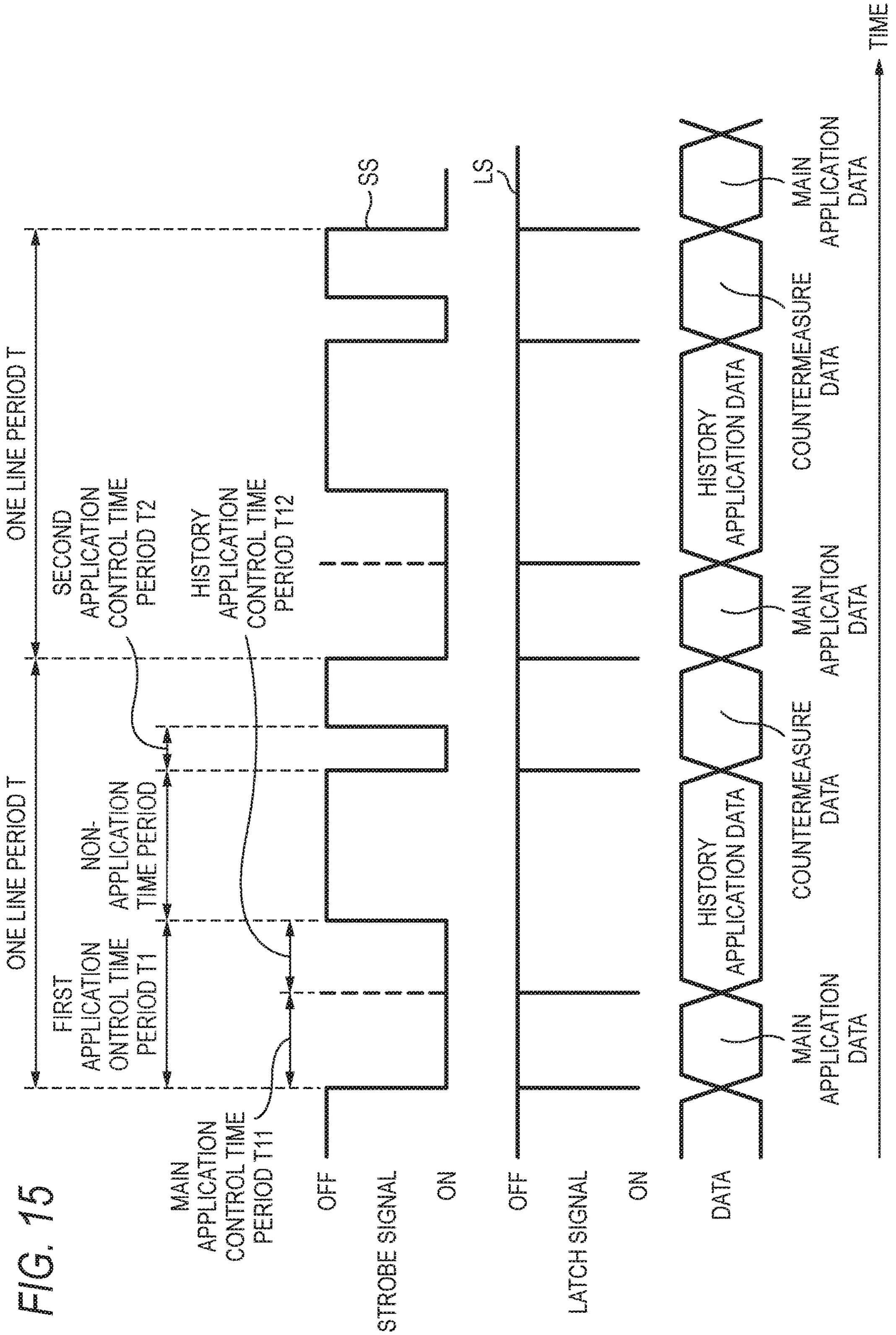
FIG. 15 illustrates a control signal.

FIG. 15 illustrates a control signal.

In the below, printing processing that is to be executed by the printing apparatus 1 is specifically described with reference to FIGS. 7 to 15.

When the printing data is input and the printing processing shown in FIG. 7 starts, the printing apparatus 1 first acquires the width of the medium to be printed M (step S100).

Herein, the control device 5 acquires the width of the medium to be printed M based on a signal from the tape width detection switch 24.

Subsequently, the printing apparatus 1 acquires data of the environment temperature around the printing apparatus 1 (step S200).

Herein, the control device 5 acquires data of the environment temperature that is output from the temperature sensor 25.

Then, the printing apparatus 1 executes specific line determination processing (step S300) shown in FIG. 8, countermeasure data generation processing (step S400) shown in FIG. 11, and line printing processing (step S500) shown in FIG. 13.

In the meantime, the specific line determination processing is performed by the estimation unit 40, the countermeasure data generation processing is performed by the data generation unit 50, and the line printing processing is performed by the head control unit 60.

In the specific line determination processing, as shown in FIG. 8, the estimation unit 40 first acquires line data of a leading line of the printing data and line data of a next line thereof (step S301, step S302).

Herein, the estimation unit 40 reads out the line data (line data for main application) of the leading line and the line data (line data for main application) of the next line from the RAM 7.

Thereafter, the estimation unit 40 compares two printing line data corresponding to two lines that are to be printed with being adjacent to each other (step S303).

Herein, the comparison unit 41 compares the printing line data of the next line acquired in step S302 and printing line data (hereinafter, referred to as 'pre-line data'. For example, the printing line data of the leading line acquired in step S301) of a line spaced by one line before the next line.

Specifically, for example, the estimation unit counts data "0xff", which indicates the printing dots to continue by 8 dots and included in each of the printing line data of the pre-line and the printing line data of the next line, and calculates a difference thereof (the number of 0xff of the leading line−the number of 0xff of the next line).

Based on the comparison result, the comparison unit 40 determines whether the next line is the specific line (step S304).

Herein, the determination unit 42 determines whether the sticking will occur at the next line, based on the comparison result of the printing line data of the pre-line and the printing line data of the next line.

Specifically, for example, the determination unit 42 refers to a threshold value table TB1 of FIG. 9 stored in the ROM 6 and acquires a threshold value corresponding to the width of the medium to be printed M acquired in step S100.

Then, when the difference (the number of 0xff of the pre-line−the number of 0xff of the next line) calculated in step S303 is equal to or greater than the threshold value acquired from the threshold value table TB1, it is determined that a possibility of occurrence of sticking is relatively high, and when the difference is smaller than the threshold value, it is determined that the possibility of occurrence of sticking is relatively low.

When it is determined that the possibility of occurrence of sticking is relatively low, processing of step S305 is skipped.

On the other hand, when it is determined that the possibility of occurrence of sticking is relatively high, the estimation unit 40 determines the specific line (step S305).

Herein, the determination unit 42 determines the next line of which the line data has been acquired in step S302, as the specific line.

Thereafter, the estimation unit 40 determines whether the next line of which the line data has been acquired in step S302 is a final line, based on the printing data (step S306).

When it is determined that the next line is a final line, the estimation unit 40 ends the specific line determination processing.

On the other hand, when it is determined that the next line is not a final line, the estimation unit repeats the processing of steps S302 to S306 until it is determined in step S306 that the next line is a final line.

By the above processing, the printing apparatus 1 (estimation unit 40) generates specific line data for specifying the specific line.

The specific line data D1 shown in FIG. 10A is an example of the specific line data that is generated when a $30^{th}$ line is estimated as the specific line.

The specific line data D2 shown in FIG. 10B is an example of the specific line data that is generated when a $30^{th}$ line and a $95^{th}$ line are estimated as the specific line.

When the specific line determination processing shown in FIG. 8 is over, the data generation unit 50 starts the countermeasure data generation processing shown in FIG. 11.

In the countermeasure data generation processing, the data generation unit 50 first sets the number of countermeasure target lines, which is the number of lines (lines to be included in the countermeasure target line group) at which a voltage is to be applied to the heat-generating elements continuously from the specific line for the second application control time period (step S401).

Herein, the line-number setting unit 51 may set the number of countermeasure target lines to the preset number of lines or may set the number of countermeasure target lines based on the environment temperature output from the temperature sensor 25.

Then, the data generation unit 50 sets a heat generation pattern (step S402).

The heat generation pattern is a combination of the heat-generating elements to which a voltage is to be applied for the second application control time period.

Herein, the pattern setting unit 52 specifies the heat-generating elements facing the medium to be printed M, based on the width of the medium to be printed M acquired in step S100, and sets the specified heat-generating elements as the heat-generating elements to which a voltage is to be applied for the second application control time period, for example.

Then, the data generation unit 50 acquires the printing line data of the leading line of the printing data (step S403).

Herein, the data generation unit 50 reads out the printing line data (printing line data for main application) of the leading line from the printing data storage part 7*a*, and sets the leading line as a current line.

Thereafter, the data generation unit 50 generates printing line data for history application (step S404).

Herein, the data generation unit 50 generates the printing line data for history application of the current line, based on the printing line data for main application acquired already, and stores the same in the printing data storage part 7*a*.

When the printing line data for history application is generated, the data generation unit 50 determines whether the current line is the specific line, based on the specific line data (step S405).

The data generation unit 50 determines that the current line is the specific line, when the specific line data is the data D1 shown in FIG. 10A and the current line is a $30^{th}$ line.

When it is determined that the current line is the specific line, the data generation unit 50 generates countermeasure line data of the current line having a heat generation pattern set in step S402 (step S406).

On the other hand, when it is determined that the current line is not the specific line, the data generation unit 50 determines whether the current line is within the number of countermeasure target lines set in step S401 from the specific line (step S407).

When it is determined in step S407 that the current line is within the number of countermeasure target lines, the data generation unit 50 generates countermeasure line data of the current line having a heat generation pattern set in step S402 (step S406).

When it is determined in step S407 that the current line is not within the number of countermeasure target lines, the data generation unit 50 generates countermeasure line data of the current line for designating non-application to all the heat-generating elements (i.e., having an empty pattern consisting of OFF) (step S408).

When the countermeasure line data is generated, the data generation unit 50 determines whether the current line is a final line (step S409).

When it is determined that the current line is a final line, the data generation unit 50 ends the countermeasure data generation processing. On the other hand, when it is determined that the current line is not a final line, the data generation unit 50 reads out printing line data (printing line data for main application) of a next line from the printing data storage part 7*a*, and sets the read line, as a current line (step S410).

Then, the data generation unit 50 repeats the processing of steps 5404 to S410 until it is determined in step S409 that the current line is a final line.

By the above processing, the countermeasure data including the same number of countermeasure line data as the number of lines to be printed is generated.

Meanwhile, FIG. 12 depicts an example of the countermeasure line data that is generated when the width of the medium to be printed M is 3.5 mm, a $30^{th}$ line is the specific line and the number of countermeasure target lines is 3.

In FIG. 12, the main application data, the history application data and the countermeasure data are shown with a black circle when the heat-generating elements 10*a* of the thermal head 10 are enabled to generate the heat (ON), and with a white circle when the heat-generating elements 10*a* are not enabled to generate the heat (OFF).

When the countermeasure data generation processing shown in FIG. 11 is over, the head control unit 60 starts the line printing processing shown in FIG. 13.

In the line printing processing, the head control unit 60 first acquires data of the head temperature of the thermal head 10, which is output from the thermistor 13 (step S501).

Then, the head control unit 60 acquires the application time from the application time table storage part 6*a* of the ROM 6 (step S502).

Herein, the head control unit 60 refers to an application time table stored in the application time table storage part 6*a* and acquires the application time corresponding to the head temperature.

Specifically, the head control unit 60 executes retrieval processing for an application time table TB1 shown in FIG. 14, for example, by using the head temperature acquired in step S501 as a key, and acquires main application time, history application time and countermeasure application time from a record corresponding to the head temperature.

When the application time is acquired, the head control unit 60 acquires the line data (line data for main application and line data for history application) and countermeasure line data from the printing data storage part 7*a* of the RAM 7 (step S503).

Then, the head control unit 60 outputs the printing line data (printing line data for main application and printing line data for history application), the countermeasure line data and the strobe signal (control signal) to the head driving circuit 9 (step S504).

Herein, the head control unit 60 generates the strobe signal corresponding to the main application time, history application time and countermeasure application time acquired in step S502, and outputs the same to the head driving circuit 9. Thereby, the head driving circuit 9 drives the thermal head 10 based on the printing line data (printing line data for main application and printing line data for history application), the countermeasure line data and the control signal (strobe signal), so that one line is printed on the medium to be printed M by the thermal head 10.

In the meantime, a strobe signal SS shown in FIG. 14 is an example of the strobe signal that is generated by the head control unit 60.

The head control unit 60 sets temporal lengths of the main application control time period T11, history application control time period T12 and second application control time period T2 of the strobe signal SS, in correspondence to the main application time, history application time and countermeasure application time acquired in step S502.

Finally, the head control unit 60 determines whether the line of which the printing line data has been acquired in step S503 is a final line (step S505).

When it is determined that the line of which the printing line data has been acquired in step S503 is a final line, the head control unit 60 ends the line printing processing. On the other hand, when it is determined that the line of which the printing line data has been acquired in step S503 is not a final line, the head control unit 60 repeats the processing of steps 5501 to 5505 until it is determined in step S505 that the line is a final line.

The printing apparatus 1 executes the printing processing shown in FIG. 7, so that it is possible to suppress the occurrence of sticking with the simple control.

In particular, as shown in FIG. 12, the countermeasure data is generated so that for the second application control time period, the voltage is to be applied to the heat-generating elements 10 continuously from the specific line by the plurality of lines. For this reason, it is possible to suppress the rapid temperature lowering after the specific line in the printing apparatus 1.

In the printing apparatus 1, the estimation unit 40 compares the printing line data adjacent to each other. For this reason, since it is possible to expect the rapid temperature lowering over the lines, it is possible to estimate the specific line with high precision.

Meanwhile, in the above example, the control device 5 is configured to determine the $n^{th}$ line, for which it is estimated that the sticking will occur, as the specific line, based on the comparison result of the at least two printing line data of the plurality of printing line data included in the printing data and corresponding to the plurality of lines to be printed continuously. However, the control device 5 may also be configured to compare three or more printing line data. In this case, it is possible to estimate the specific line with higher precision.

In the printing apparatus 1, the data generation unit 50 is configured to set the heat-generating elements, to which the voltage is to be applied for the second application control time period, based on the width of the medium to be printed M. For this reason, it is possible to avoid the useless heating of the heat-generating elements, which do not face the medium to be printed M, so that it is possible to suppress the power consumption.

The heat-generating elements facing the medium to be printed M are enabled to concurrently generate the heat, so that it is possible to efficiently supply the energy to the thermal head for the relatively short application time. Therefore, it is possible to favorably suppress the occurrence of sticking for the relatively short application time.

Meanwhile, in FIG. 8, the example where the determination as to whether the sticking will occur is performed for all the lines is shown. However, in the specific line determination processing, the determination processing may be omitted for a line within the number of countermeasure target lines from the specific line.

The reason is described. For a line within the number of countermeasure target lines from the specific line, the sticking countermeasure based on the countermeasure data is taken. Therefore, it can be determined that the possibility of occurrence of sticking is low.

[Second Illustrative Embodiment]

Figure 16:
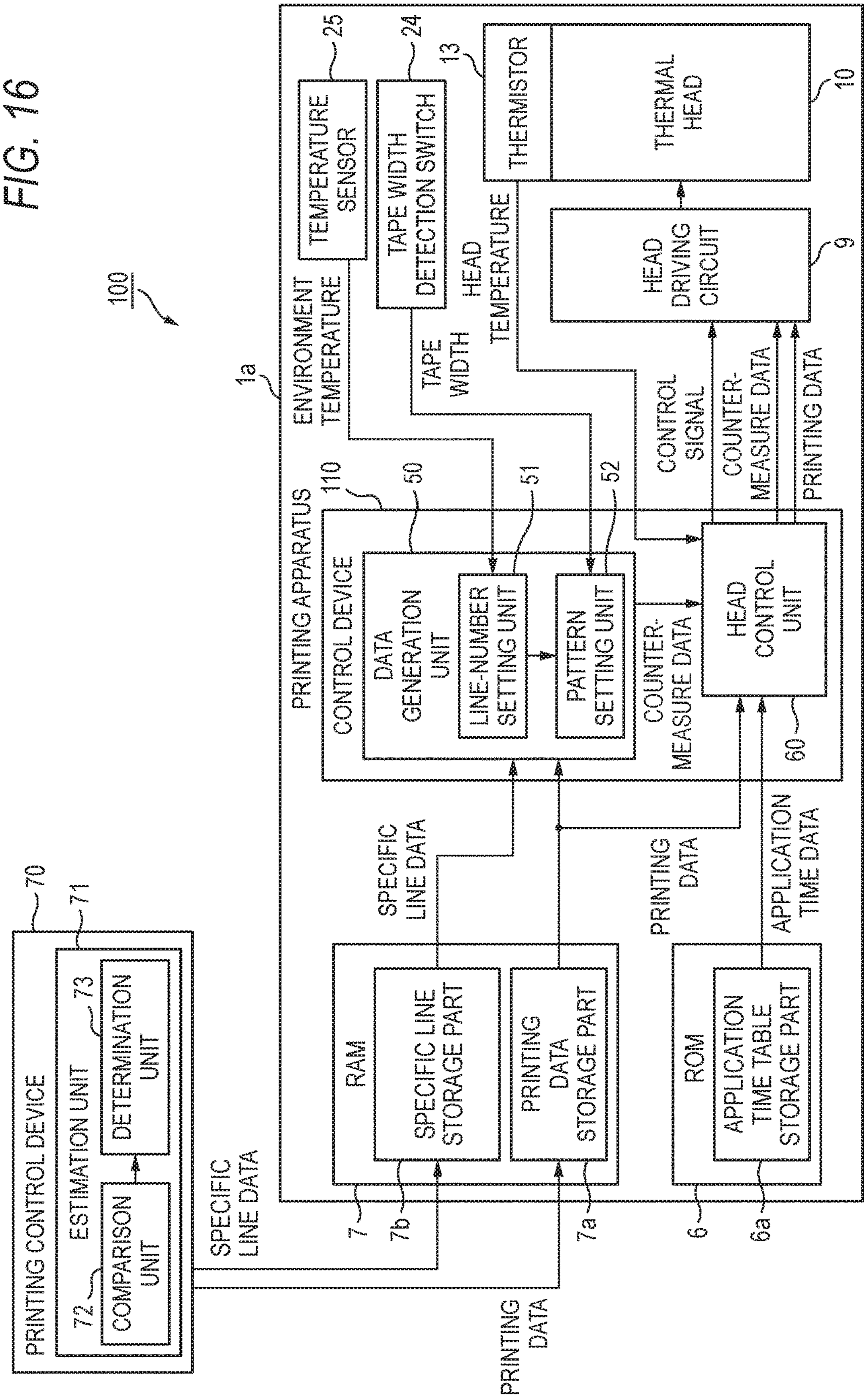
FIG. 16 exemplifies a hardware structure of a printing system 100.

FIG. 16 exemplifies a hardware structure of a printing system 100 in accordance with a second illustrative embodiment.

The printing system 100 includes a printing control device 70, and a printing apparatus 1*a*.

The printing control device 70 is provided separately from the printing apparatus 1*a*, and can exchange information with the printing apparatus 1*a*. For example, the printing control device 70 is a standard computer, and includes a processor, a memory, a storage and the like.

The printing system 100 is different from the printing apparatus 1, in that some processing of the printing apparatus 1 in accordance with the first illustrative embodiment is executed by the printing control device 70.

The printing control device 70 has an estimation unit 71 configured to function similarly to the estimation unit 40 of the printing apparatus 1 as the processor executes a program.

The estimation unit 71 has a comparison unit 72 configured to function similarly to the comparison unit 41 of the printing apparatus 1, and a determination unit 73 configured to function similarly to the determination unit 42. That is, the printing control device 70 is configured to estimate the specific line by comparing two or more printing line data, and to output the specific line data to the printing apparatus 1*a*.

In other words, the printing control device 70 is configured to determine the $n^{th}$ line, for which it is estimated that the sticking will occur, by comparing at least two printing line data of the plurality of printing line data included in the printing data and corresponding to the plurality of lines to be printed continuously, and to output the data for specifying the $n^{th}$ line, for which it is estimated that the sticking will occur, to the printing apparatus 1*a*.

The printing apparatus 1*a* is different from the printing apparatus 1, in that it has a control device 110, instead of the control device 5.

The control device 110 has the data generation unit 50 and the head control unit 60 but does not have the estimation unit 40.

For this reason, the data generation unit 50 of the printing apparatus 1*a* is configured to read out the specific line data, which is output from the printing control device 70 and is stored in the specific line data storage part 7*b*, and to generate the countermeasure data.

Also in the printing system 100 of the second illustrative embodiment, it is possible to suppress the occurrence of sticking by the simple control, like the printing apparatus 1.

[Third Illustrative Embodiment]

Figure 17:
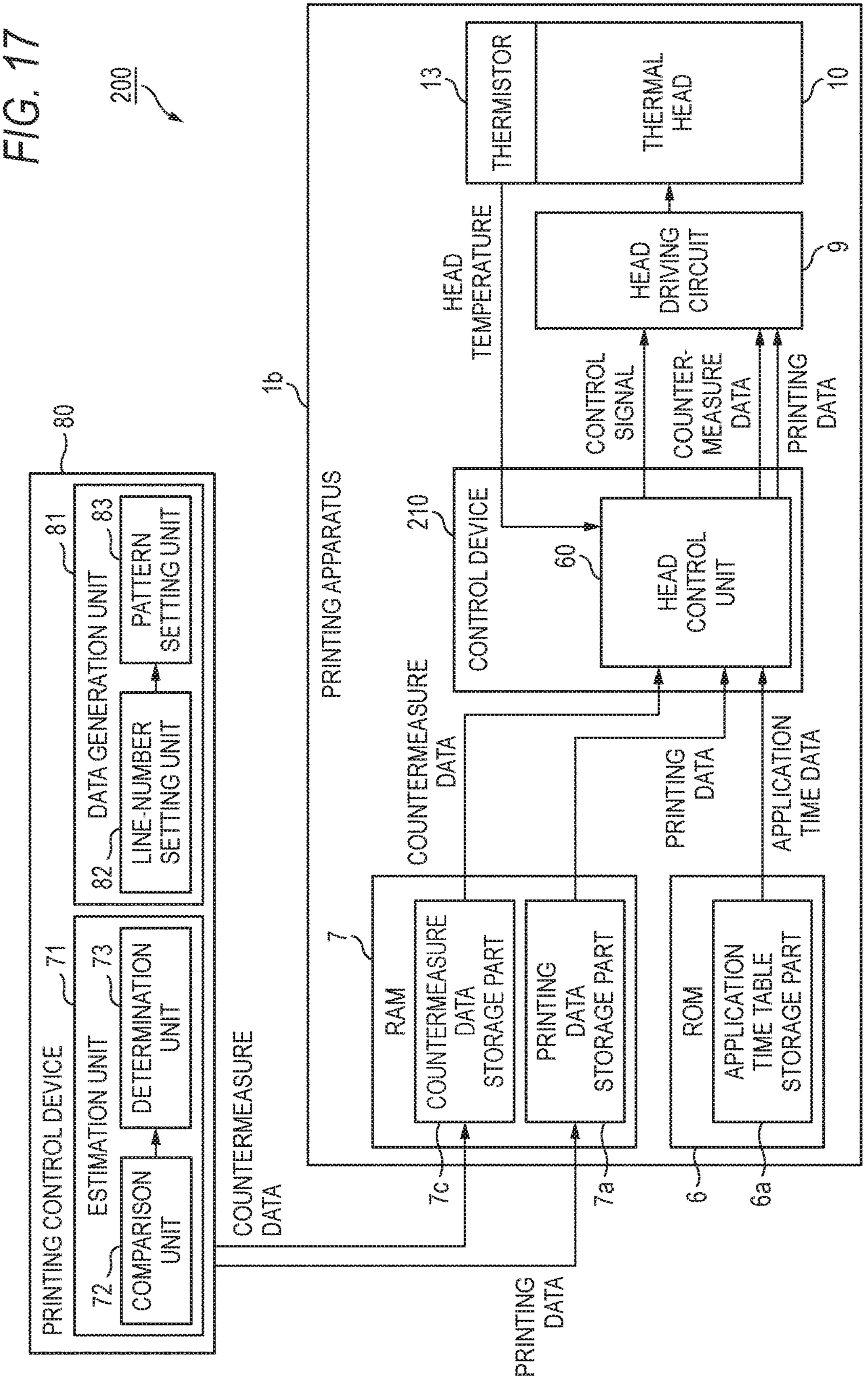
FIG. 17 exemplifies a hardware structure of a printing system 200.

FIG. 17 exemplifies a hardware structure of a printing system 200 in accordance with a third illustrative embodiment.

The printing system 200 includes a printing control device 80, and a printing apparatus 1*b*.

The printing control device 80 is provided separately from the printing apparatus 1*b*, and can exchange information with the printing apparatus 1*a*. For example, the printing control device 80 is a standard computer, and includes a processor, a memory, a storage and the like.

The printing system 200 is different from the printing apparatus 1, in that some processing of the printing apparatus 1 in accordance with the first illustrative embodiment is executed by the printing control device 80.

The printing control device 80 has an estimation unit 71 configured to function similarly to the estimation unit 40 of the printing apparatus 1 and a data generation unit 81 configured to function similarly to the data generation unit 50 of the printing apparatus 1 as the processor executes a program.

The estimation unit 71 has a comparison unit 72 configured to function similarly to the comparison unit 41 of the printing apparatus 1, and a determination unit 73 configured to function similarly to the determination unit 42.

The data generation unit 81 has a line-number setting unit 82 configured to function similarly to the line-number setting unit 51 of the printing apparatus 1, and a pattern setting unit 83 configured to function similarly to the pattern setting unit 52.

That is, the printing control device 80 is configured to estimate the specific line by comparing two or more printing line data, to generate the countermeasure data for designating the application to the heat-generating elements continuously from the specific line by the plurality of lines for the second application control time period, and to output the countermeasure data to the printing apparatus 1*b*.

The printing apparatus 1*b* is different from the printing apparatus 1, in that it has a control device 210, instead of the control device 5. The control device 210 has the head control unit 60 but does not have the estimation unit 40 and the data generation unit 50.

For this reason, the head control unit 60 of the printing apparatus 1*b* is configured to read out the countermeasure data, which is output from the printing control device 80 and is stored in the countermeasure data storage part 7*c*, and to generate the control signal.

Also in the printing system 200 of the third illustrative embodiment, it is possible to suppress the occurrence of sticking by the simple control, like the printing apparatus 1 and the printing system 100.

The above illustrative embodiments are specific examples for easily understanding the disclosure, and the disclosure is not limited thereto. The printing apparatus, the printing system, the printing control method, and the program can be diversely modified and changed without departing from the claims.

For example, when the number of heat-generating elements to be energized for printing of one line is larger than a specific number, i.e., when printing a line having printing dots exceeding the specific number on the medium to be printed M, the printing apparatus may divide and print on the line into multiple times. The above technology can be applied to the printing apparatus configured to perform the variable division printing, too.

For example, the example where the estimation unit 40 estimates the specific line by comparing the printing line data for main application has been described. However, the estimation unit 40 may be configured to estimate the specific line, in consideration of the printing line data for history application.

In the below, the inventions defined in the claims of the subject application originally filed are additionally described.

What is claimed is:

1. A printing apparatus comprising:

a thermal head that is configured to print an image on a plurality of lines in a medium; and a processor, wherein the thermal head includes a plurality of heat-generating elements configured to generate heat when a voltage is applied thereto, and the thermal head is controlled to print on the plurality of lines in the medium in setting periods, and wherein the processor is configured to:

set a second period within each of the setting periods, the second period being a time period for adjusting a temperature change of the plurality of heat-generating elements of the thermal head without printing on the medium, and the second period being set to a timing after a first period in each of the setting periods, the first period being a time period for printing on the medium;

determine a $n^{th}$ line (n: an integer of 1 or greater) among the plurality of lines in the medium based on printing data for printing the image, the nth line being a line estimated to have a possibility of sticking on the medium by the thermal head; and adjust a temperature change of at least a part of the plurality of heat-generating elements in the second periods corresponding to at least the $n^{th}$ line and a $(n+1)^{th}$ line as a target line group, the $(n+1)^{th}$ line is to be printed immediately after printing of the $n^{th}$ line based on the printing data, so as to suppress the sticking.

2. The printing apparatus according to claim 1, wherein the processor is configured to:

generate countermeasure data for adjusting the temperature change of at least a part of the plurality of heat-generating elements in the second periods so as to suppress the sticking being due to the temperature change, regardless of the printing data; and execute the determination of the $n^{th}$ line and the generation of the countermeasure data before executing the printing.

3. The printing apparatus according to claim 1, wherein the printing data includes each piece of printing line data for printing each line, and wherein the processor is configured to:

compare the at least two pieces of printing line data, and determine the $n^{th}$ line, as a specific line estimated to have a possibility of sticking, based on a result of the comparison.

4. The printing apparatus according to claim 3, wherein the processor is configured to:

compare the two pieces of printing line data corresponding to the two lines which are to be printed with being adjacent to each other; and determine the $n^{th}$ line, as the specific line, based on a result of the comparison.

5. The printing apparatus according to claim 4, wherein the processor is configured to:

compare a number of first printing dots to a number of second printing dots, wherein the first printing dots are to be specified based on one of the two pieces of printing line data and are set to be printed on the medium, and the second printing dots are to be specified based on the other of the two pieces of printing line data and are set to be printed on the medium, and determine the specific line, based on a result of the comparison.

6. The printing apparatus according to claim 4, wherein the processor is configured to:

compare a number of first printing dot groups to a number of second printing dot groups, wherein the first printing dots are specified based on one of the two pieces of printing line data and are set to be printed on the medium, and the first printing dot group is a group in which the first printing dots are continuously aligned by a preset number, and the second printing dots are specified based on the other of the two pieces of printing line data and are set to be printed on the medium, and the second printing dot group is a group in which the second printing dots are continuously aligned by a preset number, and determine the specific line, based on a result of the comparison.

7. The printing apparatus according to claim 1, further comprising:

a width detection unit that is configured to detect a width of the medium, wherein the processor is configured to:

set the heat-generating elements in the second period at each line in the target line group of the countermeasure data, based on the width of the medium detected by the width detection unit.

8. The printing apparatus according to claim 7, wherein the processor is configured to:

set the heat-generating elements located at positions facing the medium, in the second period at each line in the target line group of the countermeasure data.

9. The printing apparatus according to claim 7, wherein the processor is configured to:

set a number of the lines in the target line group, based on the width of the medium detected by the width detection unit.

10. The printing apparatus according to claim 7, further comprising:

an environment temperature measuring unit that is configured to measure a temperature around the printing apparatus, as an environment temperature, wherein the processor is configured to:

set a number of lines in the target line group, based on at least one of (i) the environment temperature, (ii) the width of the medium detected by the width detection unit and (iii) the printing data.

11. The printing apparatus according to claim 1, further comprising:

an environment temperature measuring unit that is configured to measure a temperature around the printing apparatus, as an environment temperature, wherein the processor is configured to:

set a number of lines in the target line group, based on the environment temperature.

12. A printing system comprising:

a printing apparatus that includes a thermal head configured to print an image on a plurality of lines in a medium, and a processor configured to control the printing, and a computer that is provided separately from the printing apparatus, wherein the thermal head includes a plurality of heat-generating elements configured to generate heat when a voltage is applied thereto, and the thermal head is controlled to print on the plurality of lines in the medium in setting periods, wherein the computer is configured to:

determine, as a specific line, a $n^{th}$ line (n: an integer of 1 or greater) among the plurality of lines based on printing data for printing the image, the specific line is a line estimated to have a possibility of sticking, and output specific line data for specifying the specific line to the printing apparatus, and wherein the processor is configured to:

set a second period within each of the setting periods, the second period being a time period for adjusting a temperature change of the plurality of heat-generating elements of the thermal head without printing on the medium, and the second period being set to a timing after a first period in the each of the setting periods, the first period being a time period for printing on the medium, set the $n^{th}$ line and at least one line including a $(n+1)^{th}$ line which is to be printed immediately after printing of the nth line, as a target line group based on the specific line data, and adjust a temperature change of at least a part of the plurality of heat-generating elements in the second periods corresponding to the target line group so as to suppress the sticking.

13. The printing system according to claim 12, wherein the computer is configured to execute the determination of the $n^{th}$ line, and the output of the specific line data to the printing apparatus before the printing apparatus executes the printing, and wherein the processor is configured to:

generate countermeasure data for adjusting the temperature change of at least a part of the plurality of heat-generating elements so as to suppress the sticking, regardless of the printing data, and execute the setting of the target line group and the generation of the countermeasure data before the printing apparatus executes the printing.

14. A printing system comprising:

a printing apparatus that includes a thermal head configured to print an image on a plurality of lines in a medium, a head driving unit configured to drive the thermal head, and a processor, and a computer that is provided separately from the printing apparatus, wherein the thermal head includes a plurality of heat-generating elements configured to generate heat when a voltage is applied thereto, and the thermal head is controlled to print on the plurality of lines in the medium in setting periods, wherein the processor is configured to:

set a second period within each of the setting periods, the second period being a time period for adjusting a temperature change of the plurality of heat-generating elements of the thermal head without printing on the medium, and the second period being set to a timing after a first period in the each of the setting periods, the first period being a time period for printing on the medium, drive the thermal head by the head driving unit, based on printing data for printing the plurality of lines and countermeasure data generated at the computer, and wherein the computer is configured to:

determine a $n^{th}$ line (n: an integer of 1 or greater) among the plurality of lines based on printing data for printing the image, the $n^{th}$ line being a line estimated to have a possibility of sticking the thermal head to the medium, and generate the countermeasure data for adjusting a temperature change of at least a part of the plurality of heat-generating elements in the second periods of at least two lines as a target line group so as to suppress the sticking, the at least two lines including the nth line and a (n+1)th line which is to be printed immediately after printing of the $n^{th}$ line.

15. The printing system according to claim 14, wherein the computer is configured to execute the determination of the $n^{th}$ line and the generation of the countermeasure data, before the printing apparatus executes the printing.

16. A printing control method of a printing apparatus, wherein the printing apparatus includes a thermal head which is configured to print an image on a plurality of lines in a medium, wherein the thermal head includes a plurality of heat-generating elements configured to generate heat when a voltage is applied thereto, and the thermal head is controlled to print on the plurality of lines in the medium in setting periods, and wherein the printing control method comprises:

setting a second period within each of the setting periods, the second period being a time period for adjusting a temperature change of the plurality of heat-generating elements of the thermal head without printing on the medium, and the second period being set to a timing after a first period in the each of the setting periods, the first period being a time period for printing on the medium, determining a $n^{th}$ line (n: an integer of 1 or greater) among the plurality of lines based on printing data for printing the image, the $n^{th}$ line being a line estimated to have a possibility of sticking, and adjusting a temperature change of at least a part of the plurality of heat-generating elements in the second periods of at least two lines as a target line group so as to suppress the sticking, the at least two lines including the $n^{th}$ line and a $(n+1)^{th}$ line which is to be printed immediately after printing of the $n^{th}$ line.

17. The printing control method according to claim 16, further comprising:

generating countermeasure data for adjusting the temperature change of at least a part of the plurality of heat-generating elements in the second periods so as to suppress the sticking, regardless of the printing data, wherein the determination of the $n^{th}$ line and the generation of the countermeasure data are executed before the printing apparatus executes the printing.

18. A non-transitory computer-readable recording medium having a printing control program for controlling a printing apparatus recorded therein, wherein the printing apparatus includes a thermal head which is configured to print an image on a plurality of lines in a medium, wherein the thermal head includes a plurality of heat-generating elements configured to generate heat when a voltage is applied thereto, and the thermal head is controlled to print on the plurality of lines in the medium in setting periods, and wherein the printing control program is configured to allow a computer to:

set a second period within each of the setting periods, the second period being a time period for adjusting a temperature change of the plurality of heat-generating elements of the thermal head without printing on the medium, and the second period being set to a timing after a first period in the each of the setting periods, the first period being a time period for printing on the medium, determine a $n^{th}$ line (n: an integer of 1 or greater) among the plurality of lines based on printing data for printing image, the $n^{th}$ line being a line estimated to have a possibility of sticking, and adjust a temperature change of at least a part of the plurality of heat-generating elements in the second periods of at least two lines as a target line group so as to suppress the sticking, the at least two lines including the $n^{th}$ line and a $(n+1)^{th}$ line which is to be printed immediately after printing of the $n^{th}$ line.

* * * * *